United States Patent
Hopwood et al.

(10) Patent No.: US 7,604,958 B2
(45) Date of Patent: Oct. 20, 2009

(54) SYNTHETIC MAMMALIAN α-N-ACETYLGLUCOSAMINIDASE AND GENETIC SEQUENCES ENCODING SAME

(75) Inventors: John Joseph Hopwood, Stonyfell (AU); Hamish Steele Scott, Geneva (CH); Birgit Weber, Hackney (AU); Lianne Blanch, Grange (AU); Donald Stewart Anson, Thebarton (AU)

(73) Assignee: Central Northern Adelaide Health Service, Adelaide (AU)

( * ) Notice: Subject to any disclaimer, the term of this patent is extended or adjusted under 35 U.S.C. 154(b) by 0 days.

(21) Appl. No.: 11/657,766

(22) Filed: Jan. 25, 2007

(65) Prior Publication Data

US 2007/0212769 A1    Sep. 13, 2007

Related U.S. Application Data

(60) Continuation of application No. 09/836,613, filed on Apr. 17, 2001, now abandoned, which is a division of application No. 09/077,354, filed as application No. PCT/AU96/00747 on Nov. 22, 1996, now Pat. No. 6,255,096.

(30) Foreign Application Priority Data

Nov. 23, 1995 (AU) .................... PN6748

(51) Int. Cl.
C12P 21/06   (2006.01)
C12N 9/00    (2006.01)
C12N 9/26    (2006.01)
C12N 1/20    (2006.01)
C12N 15/00   (2006.01)

(52) U.S. Cl. ............ 435/69.1; 435/183; 435/201; 435/320.1; 536/23.2

(58) Field of Classification Search ............ 435/69.1, 435/183, 201, 252.3, 320.1; 536/23.2
See application file for complete search history.

(56) References Cited

OTHER PUBLICATIONS

Bielicki et al. Biochem J. Oct. 1, 1995;311 (Pt 1):333-9.*
Siuzdak. Proc Natl Acad Sci U S A. Nov. 22, 1994;91(24):11290-7.*
Sambrook et al. Molecular cloning A Laboratory Manual, 2nd edition, Cold Spring Harbor, N.Y. 1989, pp. 8.46-8.52 and pp. 11.2-11.19.*
Chica et al. Curr Opin Biotechnol. Aug. 2005;16(4):378-84.*
Zhao et al. Protein Expr Purif. Jun. 2000;19(1):202-11.*
Li et al. Peptides. Sep. 2008;29(9):1498-504. Epub Apr. 26, 2008.*
von Heijne. Nucleic Acids Res. Jun. 11, 1986;14(11):4683-90.*
Cai et al. Peptides. Jan. 2003;24(1):159-61.*
Sasaki et al. (1991) "Purification and Partial Characterization of α-Acetylglucosaminidase from Human Liver", *J. Biochem.* 110: 842-846.
Von Figura et al. (1975) Serum α-N-Acetylglucosaminidase: Determination, Characterization, and Corrective Activity in Sanfilippo B Fibroblasts, *Z. Klin. Chem. Klin. Biochem.* 13: 285-289.
Von Figura et al. (1976) "Sanfilippo Disease Type B: Presence of Material Cross Reacting with Antibodies against α-N-Acetylglucosaminidase", *Eur. J. Biochem* 61: 581-588.
Weber et al. (1996) "Cloning and Expression of the Gene Involved in Sanfilippo B Syndrome (mucopolysaccharidosis III B)" *Hum. Mol. Gen.* 5: 771-777.
Weber et al. (2001) "Expression and Characterization of Human Recombinant and α-N-Acetylglucosaminidase", *Protein Expression and Purification*, 21: 251-259.
Zhao et al. (1994) "Sanfilippo Syndrome Type B: cDNA and Gene Encoding Human α-N-Acetylglucosaminidase", *Am. J. Gen.* 55: A252 (Abstract 1473).
Zhao et al. (1995) "The Gene Encoding α-N-Acetylglucosaminidase and Mutations Underlying Sanfilippo B Syndrome", *Am. J. Gen.* 57: A185 (Abstract 1059).
Zhao et al. (1996) "The Molecular Basis of Sanfilippo Sydrome Type B", *Proc. Nat. Acad. Sci.* 93: 6101-6105.
Zhao et al. (1996) Swissprot Accession No. P54802.

* cited by examiner

*Primary Examiner*—Christian L Fronda
(74) *Attorney, Agent, or Firm*—Ann R. Pokalsky, Esq.; Dilworth & Barrese, LLP

(57) ABSTRACT

The present invention relates generally to mammalian α-N-acetyglucosaminidase and to genetic sequences encoding same and to their use in the investigation, diagnosis and treatment of subjects suspected of or suffering from α-N-acetyglucosaminidase deficiency.

5 Claims, 2 Drawing Sheets

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 2575 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
   (A) ORGANISM: Homo sapiens
   (F) TISSUE TYPE: Peripheral Blood
   (G) CELL TYPE: Leukocyte (ix) FEATURE:
   (A) NAME/KEY: CDS
   (B) LOCATION: 102..2330

(xi) SEQUENCE DESCRIPTION: SEQ ID NO: 1:

```
CCCGGGCTTA GCCTTCGGGT CCACGTGGCC GGAGGCCGGC AGCTGATTGG ACGCGGGCCG      60

CCCCACCCCC TGGCCGTCGC GGGACCCGCA GGACTGAGAC C ATG GAG GCG GTG         113
                                             Met Glu Ala Val
                                               1

GCG GTG GCC GCG GCG GTG GGG GTC CTT CTC CTG GCC GGG GCC GGG GGC      161
Ala Val Ala Ala Ala Val Gly Val Leu Leu Leu Ala Gly Ala Gly Gly
  5                  10                  15                  20

GCG GCA GGC GAC GAG GCC CGG GAG GCG GCG GCC GTG CGG GCG CTC GTG      209
Ala Ala Gly Asp Glu Ala Arg Glu Ala Ala Ala Val Arg Ala Leu Val
                 25                  30                  35

GCC CGG CTG CTG GGG CCA GGC CCC GCG GCC GAC TTC TCC GTG TCG GTG      257
Ala Arg Leu Leu Gly Pro Gly Pro Ala Ala Asp Phe Ser Val Ser Val
         40                  45                  50

GAG CGC GCT CTG GCT GCC AAG CCG GGC TTG GAC ACC TAC AGC CTG GGC      305
Glu Arg Ala Leu Ala Ala Lys Pro Gly Leu Asp Thr Tyr Ser Leu Gly
             55                  60                  65

GGC GGC GGC GCG GCG CGC GTG CGG GTG CGC GGC TCC ACG GGC GTG GCG      353
Gly Gly Gly Ala Ala Arg Val Arg Val Arg Gly Ser Thr Gly Val Ala
 70                  75                  80

GCC GCC GCG GGG CTG CAC CGC TAC CTG CGC GAC TTC TGT GGC TGC CAC      401
Ala Ala Ala Gly Leu His Arg Tyr Leu Arg Asp Phe Cys Gly Cys His
 85                  90                  95                 100

GTG GCC TGG TCC GGC TCT CAG CTG CGC CTG CCG CGG CCA CTG CCA GCC      449
Val Ala Trp Ser Gly Ser Gln Leu Arg Leu Pro Arg Pro Leu Pro Ala
                105                 110                 115

GTG CCG GGG GAG CTG ACC GAG GCC ACG CCC AAC AGG TAC CGC TAT TAC      497
Val Pro Gly Glu Leu Thr Glu Ala Thr Pro Asn Arg Tyr Arg Tyr Tyr
            120                 125                 130

CAG AAT GTG TGC ACG CAA AGC TAC TCC TTC GTG TGG TGG GAC TGG GCC      545
Gln Asn Val Cys Thr Gln Ser Tyr Ser Phe Val Trp Trp Asp Trp Ala
        135                 140                 145

CGC TGG GAG CGA GAG ATA GAC TGG ATG GCG CTG AAT GGC ATC AAC CTG      593
Arg Trp Glu Arg Glu Ile Asp Trp Met Ala Leu Asn Gly Ile Asn Leu
    150                 155                 160

GCA CTG GCC TGG AGC GGC CAG GAG GCC ATC TGG CAG CGG GTG TAC CTG      641
Ala Leu Ala Trp Ser Gly Gln Glu Ala Ile Trp Gln Arg Val Tyr Leu
165                 170                 175                 180

GCC TTG GGC CTG ACC CAG GCA GAG ATC AAT GAG TTC TTT ACT GGT CCT      689
Ala Leu Gly Leu Thr Gln Ala Glu Ile Asn Glu Phe Phe Thr Gly Pro
                185                 190                 195

GCC TTC CTG GCC TGG GGG CGA ATG GGC AAC CTG CAC ACC TGG GAT GGC      737
Ala Phe Leu Ala Trp Gly Arg Met Gly Asn Leu His Thr Trp Asp Gly
            200                 205                 210

CCC CTG CCC CCC TCC TGG CAC ATC AAG CAG CTT TAC CTG CAG CAC CGG      785
Pro Leu Pro Pro Ser Trp His Ile Lys Gln Leu Tyr Leu Gln His Arg
        215                 220                 225

GTC CTG GAC CAG ATG CGC TCC TTC GGC ATG ACC CCA GTG CTG CCT GCA      833
Val Leu Asp Gln Met Arg Ser Phe Gly Met Thr Pro Val Leu Pro Ala
    230                 235                 240
```

-continued

| | | |
|---|---|---|
| TTC GCG GGG CAT GTT CCC GAG GCT GTC ACC AGG GTG TTC CCT CAG GTC<br>Phe Ala Gly His Val Pro Glu Ala Val Thr Arg Val Phe Pro Gln Val<br>245                             250                        255                        260 | 881 |
| AAT GTC ACG AAG ATG GGC AGT TGG GGC CAC TTT AAC TGT TCC TAC TCC<br>Asn Val Thr Lys Met Gly Ser Trp Gly His Phe Asn Cys Ser Tyr Ser<br>                               265                        270                        275 | 929 |
| TGC TCC TTC CTT CTG GCT CCG GAA GAC CCC ATA TTC CCC ATC ATC GGG<br>Cys Ser Phe Leu Leu Ala Pro Glu Asp Pro Ile Phe Pro Ile Ile Gly<br>                   280                        285                        290 | 977 |
| AGC CTC TTC CTG CGA GAG CTG ATC AAA GAG TTT GGC ACA GAC CAC ATC<br>Ser Leu Phe Leu Arg Glu Leu Ile Lys Glu Phe Gly Thr Asp His Ile<br>         295                        300                        305 | 1025 |
| TAT GGG GCC GAC ACT TTC AAT GAG ATG CAG CCA CCT TCC TCA GAG CCC<br>Tyr Gly Ala Asp Thr Phe Asn Glu Met Gln Pro Pro Ser Ser Glu Pro<br>310                             315                        320 | 1073 |
| TCC TAC CTT GCC GCA GCC ACC ACT GCC GTC TAT GAG GCC ATG ACT GCA<br>Ser Tyr Leu Ala Ala Ala Thr Thr Ala Val Tyr Glu Ala Met Thr Ala<br>325                             330                        335                        340 | 1121 |
| GTG GAT ACT GAG GCT GTG TGG CTG CTC CAA GGC TGG CTC TTC CAG CAC<br>Val Asp Thr Glu Ala Val Trp Leu Leu Gln Gly Trp Leu Phe Gln His<br>                               345                        350                        355 | 1169 |
| CAG CCG CAG TTC TGG GGG CCC GCC CAG ATC AGG GCT GTG CTG GGA GCT<br>Gln Pro Gln Phe Trp Gly Pro Ala Gln Ile Arg Ala Val Leu Gly Ala<br>         360                        365                        370 | 1217 |
| GTG CCC CGT GGC CGC CTC CTG GTT CTG GAC CTG TTT GCT GAG AGC CAG<br>Val Pro Arg Gly Arg Leu Leu Val Leu Asp Leu Phe Ala Glu Ser Gln<br>                        375                        380                        385 | 1265 |
| CCT GTG TAT ACC CGC ACT GCC TCC TTC CAG GGC CAG CCC TTC ATC TGG<br>Pro Val Tyr Thr Arg Thr Ala Ser Phe Gln Gly Gln Pro Phe Ile Trp<br>         390                        395                        400 | 1313 |
| TGC ATG CTG CAC AAC TTT GGG GGA AAC CAT GGT CTT TTT GGA GCC CTA<br>Cys Met Leu His Asn Phe Gly Gly Asn His Gly Leu Phe Gly Ala Leu<br>405                             410                        415                        420 | 1361 |
| GAG GCT GTG AAC GGA GGC CCA GAA GCT GCC CGC CTC TTC CCC AAC TCC<br>Glu Ala Val Asn Gly Gly Pro Glu Ala Ala Arg Leu Phe Pro Asn Ser<br>                               425                        430                        435 | 1409 |
| ACC ATG GTA GGC ACG GGC ATG GCC CCC GAG GGC ATC AGC CAG AAC GAA<br>Thr Met Val Gly Thr Gly Met Ala Pro Glu Gly Ile Ser Gln Asn Glu<br>                   440                        445                        450 | 1457 |
| GTG GTC TAT CCT CTC ATG GCT GAG CTG GGC TGG CGA AAG GAC CCA GTG<br>Val Val Tyr Pro Leu Met Ala Glu Leu Gly Trp Arg Lys Asp Pro Val<br>                   455                        460                        465 | 1505 |
| CCA GAT TTG GCA GCC TGG GTG ACC AGC TTT GCC GCC CGG CGG TAT GGG<br>Pro Asp Leu Ala Ala Trp Val Thr Ser Phe Ala Ala Arg Arg Tyr Gly<br>470                             475                        480 | 1553 |
| GTC TCC CAC CCG GAC GCA GGG GCA GCG TGG AGG CTA CTG CTC CGG AGT<br>Val Ser His Pro Asp Ala Gly Ala Ala Trp Arg Leu Leu Leu Arg Ser<br>485                             490                        495                        500 | 1601 |
| GTG TAC AAC TGC TCC GGG GAG GCC TGC AGG GGC CAC AAT CGT AGC CCG<br>Val Tyr Asn Cys Ser Gly Glu Ala Cys Arg Gly His Asn Arg Ser Pro<br>                   505                        510                        515 | 1649 |
| CTG GTC AGG CGG CCG TCC CTA CAG ATG AAT ACC AGC ATC TGG TAC AAC<br>Leu Val Arg Arg Pro Ser Leu Gln Met Asn Thr Ser Ile Trp Tyr Asn<br>         520                        525                        530 | 1697 |
| CGA TCT GAT GTG TTT GAG GCC TGG CGG CTG CTC CTC ACA TCT GCT CCC<br>Arg Ser Asp Val Phe Glu Ala Trp Arg Leu Leu Leu Thr Ser Ala Pro<br>                               535                        540                        545 | 1745 |
| TCC CTG GCC ACC AGC CCC GCC TTC CGC TAC GAC CTG CTG GAC CTC ACT<br>Ser Leu Ala Thr Ser Pro Ala Phe Arg Tyr Asp Leu Leu Asp Leu Thr<br>550                             555                        560 | 1793 |

```
CGG CAG GCA GTG CAG GAG CTG GTC AGC TTG TAC TAT GAG GAG GCA AGA    1841
Arg Gln Ala Val Gln Glu Leu Val Ser Leu Tyr Tyr Glu Glu Ala Arg
565                 570                 575                 580

AGC GCC TAC CTG AGC AAG GAG CTG GCC TCC CTG TTG AGG GCT GGA GGC    1889
Ser Ala Tyr Leu Ser Lys Glu Leu Ala Ser Leu Leu Arg Ala Gly Gly
                585                 590                 595

GTC CTG GCC TAT GAG CTG CTG CCG GCA CTG GAC GAG GTG CTG GCT AGT    1937
Val Leu Ala Tyr Glu Leu Leu Pro Ala Leu Asp Glu Val Leu Ala Ser
                    600                 605                 610

GAC AGC CGC TTC TTG CTG GGC AGC TGG CTA GAG CAG GCC CGA GCA GCG    1985
Asp Ser Arg Phe Leu Leu Gly Ser Trp Leu Glu Gln Ala Arg Ala Ala
            615                 620                 625

GCA GTC AGT GAG GCC GAG GCC GAT TTC TAC GAG CAG AAC AGC CGC TAC    2033
Ala Val Ser Glu Ala Glu Ala Asp Phe Tyr Glu Gln Asn Ser Arg Tyr
630                 635                 640

CAG CTG ACC TTG TGG GGG CCA GAA GGC AAC ATC CTG GAC TAT GCC AAC    2081
Gln Leu Thr Leu Trp Gly Pro Glu Gly Asn Ile Leu Asp Tyr Ala Asn
645                 650                 655                 660

AAG CAG CTG GCG GGG TTG GTG GCC AAC TAC TAC ACC CCT CGC TGG CGG    2129
Lys Gln Leu Ala Gly Leu Val Ala Asn Tyr Tyr Thr Pro Arg Trp Arg
                665                 670                 675

CTT TTC CTG GAG GCG CTG GTT GAC AGT GTG GCC CAG GGC ATC CCT TTC    2177
Leu Phe Leu Glu Ala Leu Val Asp Ser Val Ala Gln Gly Ile Pro Phe
            680                 685                 690

CAA CAG CAC CAG TTT GAC AAA AAT GTC TTC CAA CTG GAG CAG GCC TTC    2225
Gln Gln His Gln Phe Asp Lys Asn Val Phe Gln Leu Glu Gln Ala Phe
        695                 700                 705

GTT CTC AGC AAG CAG AGG TAC CCC AGC CAG CCG CGA GGA GAC ACT GTG    2273
Val Leu Ser Lys Gln Arg Tyr Pro Ser Gln Pro Arg Gly Asp Thr Val
710                 715                 720

GAC CTG GCC AAG AAG ATC TTC CTC AAA TAT TAC CCC GGC TGG GTG GCC    2321
Asp Leu Ala Lys Lys Ile Phe Leu Lys Tyr Tyr Pro Gly Trp Val Ala
725                 730                 735                 740

GGC TCT TGG TGATAGATTC GCCACCACTG GGCCTTGTTT TCCGCTAATT           2370
Gly Ser Trp

CCAGGGCAGA TTCCAGGGCC CAGAGCTGGA CAGACATCAC AGGATAACCC AGGCCTGG   2430

GGAGGCCCCA CGGCCTGCTG GTGGGGTCTG ACCTGGGGGG ATTGGAGGGA AATGACCT   2490

CCTCCACCAC CACCCAAAGT GTGGGATTAA AGTACTGTTT TCTTTCCACT TAAAAAAA   2550

AAAAAAGTCG AGCGGCCGCG AATTC                                      2575

(2) INFORMATION FOR SEQ ID NO: 2:

(i) SEQUENCE CHARACTERISTICS:
        (A) LENGTH: 743 amino acids
        (B) TYPE: amino acid
        (D) TOPOLOGY: linear (ii) MOLECULE TYPE: protein (ix) FEATURE:
        (A) NAME/KEY: Potentially-glycosylated Asn site,
        (B) LOCATION: 261

(ix) FEATURE:
        (A) NAME/KEY: Potentially-glycosylated Asn site,
        (B) LOCATION: 272

(ix) FEATURE:
        (A) NAME/KEY: Potentially-glycosylated Asn site,
        (B) LOCATION: 435
```

-continued

```
    (ix) FEATURE:
         (A) NAME/KEY: Potentially-glycosylated Asn site,
         (B) LOCATION: 503

(ix) FEATURE:
         (A) NAME/KEY: Potentially-glycosylated Asn site,
         (B) LOCATION: 513

(ix) FEATURE:
         (A) NAME/KEY: Potentially-glycosylated Asn site,
         (B) LOCATION: 526

(ix) FEATURE:
         (A) NAME/KEY: Potentially-glycosylated Asn site,
         (B) LOCATION: 532

(xi) SEQUENCE DESCRIPTION: SEQ ID NO: 2:

Met Glu Ala Val Ala Val Ala Ala Val Gly Val Leu Leu Leu Ala
 1               5                  10                  15

Gly Ala Gly Gly Ala Ala Gly Asp Glu Ala Arg Glu Ala Ala Val
                20                  25                  30

Arg Ala Leu Val Ala Arg Leu Leu Gly Pro Gly Pro Ala Ala Asp Phe
            35                  40                  45

Ser Val Ser Val Glu Arg Ala Leu Ala Ala Lys Pro Gly Leu Asp Thr
 50                  55                  60

Tyr Ser Leu Gly Gly Gly Ala Ala Arg Val Arg Val Arg Gly Ser
 65                  70                  75                  80

Thr Gly Val Ala Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
                100                 105                 110

Pro Leu Pro Ala Val Pro Gly Glu Leu Thr Glu Ala Thr Pro Asn Arg
            115                 120                 125

Tyr Arg Tyr Tyr Gln Asn Val Cys Thr Gln Ser Tyr Ser Phe Val Trp
            130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe
            180                 185                 190

Phe Thr Gly Pro Ala Phe Leu Ala Trp Gly Arg Met Gly Asn Leu His
            195                 200                 205

Thr Trp Asp Gly Pro Leu Pro Pro Ser Trp His Ile Lys Gln Leu Tyr
210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
            260                 265                 270

Cys Ser Tyr Ser Cys Ser Phe Leu Leu Ala Pro Glu Asp Pro Ile Phe
            275                 280                 285

Pro Ile Ile Gly Ser Leu Phe Leu Arg Glu Leu Ile Lys Glu Phe Gly
            290                 295                 300

Thr Asp His Ile Tyr Gly Ala Asp Thr Phe Asn Glu Met Gln Pro Pro
305                 310                 315                 320
```

-continued

```
Ser Ser Glu Pro Ser Tyr Leu Ala Ala Ala Thr Thr Ala Val Tyr Glu
            325                 330                 335

Ala Met Thr Ala Val Asp Thr Glu Ala Val Trp Leu Leu Gln Gly Trp
        340                 345                 350

Leu Phe Gln His Gln Pro Gln Phe Trp Gly Pro Ala Gln Ile Arg Ala
            355                 360                 365

Val Leu Gly Ala Val Pro Arg Gly Arg Leu Leu Val Leu Asp Leu Phe
        370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
                435                 440                 445

Ser Gln Asn Glu Val Val Tyr Ser Leu Met Ala Glu Leu Gly Trp Arg
        450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
        515                 520                 525

Ile Trp Tyr Asn Arg Ser Asp Val Phe Glu Ala Trp Arg Leu Leu Leu
        530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
        595                 600                 605

Val Leu Ala Ser Asp Ser Arg Phe Leu Leu Gly Ser Trp Leu Glu Gln
        610                 615                 620

Ala Arg Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
        675                 680                 685

Gly Ile Pro Phe Gln Gln His Gln Phe Asp Lys Asn Val Phe Gln Leu
        690                 695                 700

Glu Gln Ala Phe Val Leu Ser Lys Gln Arg Tyr Pro Ser Gln Pro Arg
705                 710                 715                 720
```

```
Gly Asp Thr Val Asp Leu Ala Lys Lys Ile Phe Leu Lys Tyr Tyr Pro
            725                 730                 735

Gly Trp Val Ala Gly Ser Trp
            740

(2) INFORMATION FOR SEQ ID NO: 3:

(i) SEQUENCE CHARACTERISTICS:
        (A) LENGTH: 10380 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Homo sapiens (viii) POSITION IN GENOME:
        (A) CHROMOSOME/SEGMENT: Chromosome 17

(ix) FEATURE:
        (A) NAME/KEY: exon 1
        (B) LOCATION: 990..1372

(ix) FEATURE:
        (A) NAME/KEY: exon 2
        (B) LOCATION: 2115..2262

(ix) FEATURE:
        (A) NAME/KEY: exon 3
        (B) LOCATION: 3056..3202

(ix) FEATURE:
        (A) NAME/KEY: exon 4
        (B) LOCATION: 3387..3472

(ix) FEATURE:
        (A) NAME/KEY: exon 5
        (B) LOCATION: 5667..5923

(ix) FEATURE:
        (A) NAME/KEY: exon 6
        (B) LOCATION: 7745..8955

(xi) SEQUENCE DESCRIPTION: SEQ ID NO: 3:

ATAATGAGCA GTGAGGACGA TCAGAGGTCA CCTTCCTGTC TTGGTTTTGG CAGGTTTTGA      60

CCAGTTTCTT TGCTGCATTC TGTTTTATCA GCGGGGTCTT GTGACCTTTT ATCTTGTGC     120

GACCTCCTGT CTCATCCTGT GACGAAGGCC TAACCTCCTG GGAATTCAGC CCAGCAGGT     180

TCTGCCTCAT TTTACCCAGC CCCTGTTCAA GATGGAGTCG CTCTGGTTGG AAACTTCTG     240

CAAAATGACA GCTCCTGTTA TGTTGCTGCT GCTGCCGCCA ATGGACAGCC TTTAACGTG     300

CCGCCAGCCC TGCTCCACCG CCGGCCTGGG CTCACATGGC CCCATCCCTC CTCGAACCT     360

CTAGCCTGTT AGTTACTCAA ATCTGCAAGC TCTCTGCCTT CTCAGGGCCT TCAATAAAT     420

CATTTCTTCT GTCTGGAAGG CTCTTCCTTT CCCTCTTCTA GCCAATTCCT ATTCATCCC     480

GAGTTTCAGA TTAAAAGTCA CTTCCTTTGG AAACCTTACT TCGCTACTTC GCTACTTAC     540

GCACTACTTC GCAGCATCAC AACTATGATG GAAATCCTTA CTTACGTTAA ATATCTGGT     600

TCTAGGTCAC CTCCCTGACG GGGACGGTAG GGACCGTCTT CTCGTTCATC AGTAGGGAA     660

TAGCTATGGC AGTGCCTGAT ACAAAATAAA CTCCAAATGT GTATTTATTA GATGGTTGG     720

TGGAAGTTAT TTGCGTGTGA AAGCGCGTTT TACCCGAAGG CGCTCTGTGA GGGCCAGCG     780

GTCCCCTTCG GCCCTGGAGC CGGGGTCACA CGCTCCCCAC CGCGTGCGGT CACGAGACG     840

CCCCAAGGGA GTATCCTGGT ACCCGGAAGC CGCGACTCCT GGCCCTGAGC CCGGGCTTA     900
```

-continued

```
CCTTCGGGTC CACGTGGCCG GAGCCGGCAG CTGATTGGAC GCGGGCCGCC CCACCCCCT      960
GCCGTCGCGG GACCCGCAGG ACTGAGACCA TGGAGGCGGT GGCGGTGGCC GCGGCGGT      1020
GGGTCCTTCT CCTGGCCGGG GCCGGGGGCG CGGCAGGCGA CGAGGCCCGG GAGGCGGC      1080
CCGTGCGGGC GCTCGTGGCC CGGCTGCTGG GGCCAGGCCC CGCGGCCGAC TTCTCCGT      1140
CGGTGGAGCG CGCTCTGGCT GCCAAGCCGG GCTTGGACAC CTACAGCCTG GGCGGCGG      1200
GCGCGGCGCG CGTGCGGGTG CGCGGCTCCA CGGGCGTGGC GGCCGCCGCG GGGCTGCA      1260
GCTACCTGCG CGACTTCTGT GGCTGCCACG TGGCCTGGTC CGGCTCTCAG CTGCGCCT      1320
CGCGGCCACT GCCAGCCGTG CCGGGGGAGC TGACCGAGGC CACGCCCAAC AGGTACCG      1380
CCGAAGCTTC CCCGCGTCCG CCCGAGGCGC TTACCCCCTC CCGGAGCCGC TGCCACCC      1440
ATCGGGAGGC TGAGCGGGGA GCGCTGGCCG GAAGGCCCAG CTGCGCCGCC TCCAGCAG      1500
GTGTGGCCTT GAGCCAGCCA CTCTGCCTTT CAGAGCCTCG GCTGGCCCAC CTGAAAAA      1560
GAAAGAAGAC GCCTACCGTG CAGTGTTATT GTGAGGATTT GCACGATGAT GGGCATAG      1620
TTTGTGGTGC ACAATTGGTG ATGAGTGAAT TTTCTTGCCT TCCTCCCCCA CCTTCTCT      1680
GAACCTGCGG ACTGAGGAAG GACGCCTCCA TCCCCCACCC TACAGGCCTG TGTTCCAG      1740
CCTGCCACAC TATGGAGTGA TGTGTTCACA CAGCTGTCCT CCCCTGCCCA TCTGTTAG      1800
TGTGGGGCA GGGATTCCCC GTTCCAGGAA AACACCGTGC AGAGGAGGGG CTCTGGCA       1860
GTGGCATGAA AGTGGAATAT GCCACCCAAA TACCCGCCAG GCTAGAGGGC CCTGGGAG      1920
TGCAGGGGAC GAGTGCCTCA GAAGCCCAGC CCCGGTACCT GGTCTCAGCT CCACCTGG      1980
TGGGTCCCAG TGTGCAGCAG AAGGGCCGAG TTTGGAGCCC CTCCCCTCTC CTCTAGGT      2040
GGGATGGGGG ATTTGTTCCA GGGCCGTGGA CCCTCCAGGG TGGGATGCGC CCCTGCTC      2100
GACACTGCCC GCAGGTACCG CTATTACCAG AATGTGTGCA CGCAAAGCTA CTCCTTCG      2160
TGGTGGGACT GGGCCCGCTG GGAGCGAGAG ATAGACTGGA TGGCGCTGAA TGGCATCA      2220
CTGGCACTGG CCTGGAGCGG CCAGGAGGCC ATCTGGCAGC GGGTGCGTGC CCACTGTC      2280
TTCCCCACCC TCCTCTATGG CGGGAGCCAC CGTAGGTGTT TCACCCGCC CCCCAGCA       2340
GGCGCAGTGT CTCTCTCTAG AAGTGCTTTC AGCGTGCACA GTGGCTTGGG CCTCCTAA      2400
ACTGAGGCTT CCGGCCGGGC GCGGTGGCTC ACGCCTGTCA TCCCAGCACT TCGGAGG       2460
TAGGCGGGCG GATCAGGAGT TCAGGAGATC GAGACCATCC TGGCCAACAT TGTGAAAC      2520
CGTCTCTACT AAAATACAAA GAAATAGCAA CCTGGGCAAC AGAGCGAGAC TCTGTCTA      2580
AAAAAAAAA AAAAAAACTG AGGCTTCCAG TTTGAGGAGT GGGGCTCCTT CCCCCATC       2640
CCCTATGCAG CCAATCACCT GGTCCCTTGG ATCCAACTCA TGGGCAGCTC TAGATCTG      2700
TCCCTGGAAG CTTCTGTGCT GCAATGGCTG CTCCAGGCTC TGCTTAAGCT CTTCACAC      2760
TTGCCCTGCC CTTCCATCTG GCACTCTTGC TCCATGAAGC CTTCTAAGGC CTTCCTGT      2820
GGGGAAAGCC CCTTTGTGCC CCATCTCCTC ACCCATGCGA CAAAGGCAAC ACAGTGAA      2880
CACCTACTCA CAGGTCTCTT TCCTCTGGGC TGTGGGCTCC TTGATGGCAG CGTTCGGA      2940
TTGTCTCAGT AGCCCTAGCA CCCAGCACAA AGAAGCAATG AGTGAATGGT TGTTGAAT      3000
ATGAATGAAT GAATGAAGAT GAATATATTT CTATGTGTGG GCCCTTCTTC CTCAGGTG      3060
CCTGGCCTTG GGCCTGACCC AGGCAGAGAT CAATGAGTTC TTTACTGGTC CTGCCTTC      3120
GGCCTGGGGG CGAATGGGCA ACCTGCACAC CTGGGATGGC CCCTGCCCC CTCCTGG        3180
CATCAAGCAG CTTTACCTGC AGGTAAAAGG ATGGAAAAGG GAAGGGGCAG AATCGGTG      3240
AGATGGTCAT GGGCCCAGGA AGGGTGGTAT TAGGCCGGCC CCAGGGCTCT TAACTGAG      3300
```

```
GGGGGGCTGC GTGTATCCTG GGAGATGAGG GCCTTCTCAT AGGACAGCAG TGGCCATG      3360

CACCACCCTT CCTTCTGTTC CTCCAGCACC GGGTCCTGGA CCAGATGCGC TCCTTCGG      3420

TGACCCCAGT GCTGCCTGCA TTCGCGGGGC ATGTTCCCGA GGCTGTCACC AGGTGAGG      3480

CCGCTCACCC CCTCCACTTA GCTCAGAGAG GGAATTTTAT TCCCTTCTAG AACATGAC      3540

AAAAACTTAA GCTCTGGGCC GGGCGCAGTG GCTCACGCCT GTAATCCCAG CACTTTGG      3600

GGCCGAGTTG GGCGGATCAC CTGAGGTCAG GAGTTCGAGA CCAGCCTGGC CAACATGG      3660

AAACCCTGTC TCTACTAAAA ATATAAAAAT TAGCTGGGCA TGGTGGCACG CGCCTGTA      3720

CCCATCTACT TAGGAGGCTG AGACAGGAGA ATTGCTTAAA CCTGGGAGGC AGACGTTG      3780

GTGAGTCAAG ATCACGCCAT TGCACTCCAG CCTGGGTGAC GAGCGAAACT CTGTCTCA      3840

CAAACAAACA AGCTCTGGAC GTAGGCCTGG GTTTGATTTC TGACTCTGCT ACTAATTA      3900

TGTGTGACTT CGGGCAGATG ACATGACTGC TCTGTGCCTC AGTTCCTTA CTTGTAAA       3960

GGGATCTCTA CCCACTTCGC TGTAGGGTTT GTAATTATCT CTCGATCTAT CTGTGACT      4020

GCACAGAGTG CTAGCAAATG CAGCCCTTG GGAGTGGCAG CAGGGGTGCT CCAGTGTC       4080

TTGTCCCTCC TGTTCCTCTG TGCTTCCCAG CCATCCTCTC ACATGTGGTT GGGAAAAG      4140

TTCAAGGCTC ACCTGAGACC TCCCCTCCTT CAGGAAGCCT TGCTAGTGCC CCGCATGA      4200

TCCTTTGCAC CTGCTAATGT CTGGCTCCCA TACTCTCGTA GGACTTAATG CATGCCAG      4260

GCCTCCCTGC CCGCCTCTTT GCCCCCATCA CCAGGTGGCA GGAAACTCAC TCATTCAT      4320

AATAAACTTG GTCCAGCTGT CTGAGGCTGC CAGAACTGGC TGTGCTGGGT CCTGGGAG      4380

GGCAAGAAAG GTGCCCAAGG GCTTACCCCT GATAGGAGAG ATATGTTGGC TGAAGGAT      4440

AATGTGGGGA CAAGGACAGG AATATATGTG GGTTCCGCTC TCCTCTGCCG GGAGAGAG      4500

GCAGGAAGGG CTCAGGGCAG AGCCCAGCCT TGAAAAATGA GTGTTGCTTG GACGGACG      4560

TGGCTAATGC TTGTAATCCT AGCGTTTTGG GAGGCTGAGG CGTATGGATC ACCTGCGG      4620

AGGAGTTAAA GACCAGCCTG GCCAACATGG CGAAACCCCA TCTCTACTAA AAGTACAA      4680

ATTAGCCAGG CGTGGTGGCG GGCTCCTGTA ATCCCAGCTA CTCGGTAGGC TGAGGCAT      4740

GAATCTCTTG AAGCCAGGGG CCAGAGACTG CAGTGAGCCG AGATCACACC ACTTCACT      4800

AGCCTGGGTG ACAGAGTGAG ACTCCGTCTC AAAAAAAAA AAAAAAAAAG GAAAGAAA       4860

TAAACACCTC ATGTTCTCAC TCATAGTGGG AGTTGAACAA TGAGAACAAC ATGGACAC      4920

GAAGGGAAC ATCACACACC GGGGCCTTTC GCGGTGTGGG GGTCAAGGGG AGGAGTAG       4980

TTGGGACAGA TACTTAATGC ATGCGGGGCT GAAAACCTAG ATGATGGGTT GATGGGTG      5040

GCAAACCACC ATGGCACATG TATACCTATG CAACAAACCT GCATGTTCTG CACAGAAC      5100

AACTGAAAGT ATAATTAAAA AAAAAAAAA AAGCTGGGTG CGGTGGCCCA CACCTGTA       5160

CCCAGCACTT TGGGAGGCCG AGACGGGCGG ATCACAAGGT CAGCAGATCG AGACCATC      5220

GGCTAACACA GTGAAACTCA GTCTCTACTA AAAATACAAA AAATTAGCCG GGTGTGGT      5280

CGGGCACCTG TAGTCCCAGC TACTAGGGAG GCTGAGGCAG GAGAATGGCA TGAACCTG      5340

AGGCAGAGCT TGCAGTGAGC TGAGAATGCG CCACTGCACT CCAGCCTGGG GACAGAG       5400

AGACTCTGCC TCAAAAAAAA AAAAAAAAG AAAGAAAAG GAGCGTTGCT TGTTTCAG        5460

CACAGGAAGG GGAGAGATAG TGAAAGTTTT TCAGAGAAGG TGGCCAGGGA AGGAGAAG      5520

AGGACTGTAG GCAGAGAGCA TAGCCTGTAC AAAGCCATAG AGGCAAGAGA AACCAGGA      5580

TGTAGAGAAG TTGGCAAGGC TGTTGAACAC TATGGTGAAC ACTATGGCGG CTTCCATG      5640

ATATCTGAGC TTTTGCTCCC CACTAGGGTG TTCCCTCAGG TCAATGTCAC GAAGATGG      5700
```

```
AGTTGGGGCC ACTTTAACTG TTCCTACTCC TGCTCCTTCC TTCTGGCTCC GGAAGACC      5760

ATATTCCCCA TCATCGGGAG CCTCTTCCTG CGAGAGCTGA TCAAAGAGTT TGGCACAG      5820

CACATCTATG GGGCCGACAC TTTCAATGAG ATGCAGCCAC CTTCCTCAGA GCCCTCCT      5880

CTTGCCGCAG CCACCACTGC CGTCTATGAG GCCATGACTG CAGGTACAGT GCCTGGGT      5940

GGTGGGAGAG CCCCCCAGAC CCTCAAAAAG AAGGGAGTAG CAGATGTCAG TAGGGGTA      6000

CAGAGGGACT GGAATAATGC CTCGCCATAA CACACAGTAC TTTATAGTTT ACCAAGCA      6060

TGTACACATG CGTTGTCTCA GTGAATCCCA CTGTGGTTGA GAGGTGAGCT CTGGAAGC      6120

ACAACCTGGG TCACACCTCG CGCTCCTATT TCCTGGCCGT GTGACTTATG ACTCATGA      6180

TCCTTCCCAG TGTCTCGTTT GCTTTTCCTG TAAACTGGGA CTACCTCATA GGTAGAAT      6240

CGCCTGGCCC AGAGCAAAGG CCACTAAGAG CTAGCTATGA ACAAGGATTT TGTTTCAT      6300

CTGCGTGGTT GCTGAAGTAG GCACTGCAGG CAGGAGGTGA GTGGATGTGC CTAAAGGC      6360

TAAGTGCGCA TCCTGCTACA AAACTGTGAA GCCAGGGCTC CTTCCTGCCA CTTAAAGG      6420

GAGTGGAGCA GAGGGCGCCC AAGTCAGGAA TGACTTAGTG GAGAGGCGTC TGTGTTGG      6480

AGGAAGGGAA CAGATCAGCT CAGCCTTTCT TGAGCAGTAC TGCTCCAAGT GTGACCCA      6540

ACCAGCAGCA GCAGCAGCAG CAGCCCGAGC TGTGAGATGG CAAATTCTCA GGCCCTAC      6600

AAGACCTGAA GGAGAAGCTA CATTTTTTTT TTTTTTGAGA CAGATTTCAC TCTGTTGC      6660

AGGCTGGAGC ACAGTGGCAC AATCTCATCT CACTGCAACC TTCGTCTCCT AGGTTCAA      6720

GATTCTCCTG CCTCAGCCTC CCGAGTAGCT GGGACTATAG GCACCCGCCA CCACGCCC      6780

CAATTTTTGT TTGTTTTGAG ATAGAGTCTC GCTCTGTCAC CCAGGCTGGA GTGCAGTG      6840

ACGATCTCAG TTCACTGCAA CCTCTGCTTC CTGAGTTCAA GCGATTCTCC TGCCTCAG      6900

TCCTGAGTAG CTGGGATTAC AGGCGCCCCC CAACCACACT CGGCTAATTT TTGTATTT      6960

AGTAGAGACG GGGTTTCGCT ATGTAGGTCA AGCTGGTTTC AAACTCCTGA CCTCAAAT      7020

TTCGCCCACT TCAGCCTCCC AAAGTGCTGG GATTACAGGT GTGAGCCACC TTGCCTGG      7080

AATTTTTGTA TTTTTAGTAG AAACAGGTTT CACCATGGTG GCCAGACTGG TCTCAAAC      7140

CTGACCTCAG GTGAACTGCC CACCTCAGCC TCCCAAAGTA CTGGTATTAC AGGCGTGA      7200

CACTGCGACT GGCCTTGATT TTGTTTTTGA GACAGAATCT TACTCTGTCG CCCAGACT      7260

AGTGCAGTGG CACAATCTCA GCTCACTGCA ACTTCTGCCT CATGGGTTCA AGTGATTC      7320

GTGCCTCTAC CTCCCGAGTA GCCGGGATTA CAGGCACCTG CCATTACGCT AGGCTAAT      7380

TTGTATTTTT AGTATAGACA GGGTTTCCCC ACATTGGCCA GGCTGGTCTG GAACTCCT      7440

GCTCAAGTGA TCCACCTGCT TCAGCCCCTC AGAGTACTGG GATTATAGGT GTGGGCCA      7500

ACGCCCATTC AGAAACCTCC ATGTTTTAAG GAGCCCTCTG GGTAACTCTC ATGTTCAC      7560

AAGCTGCTGA ACCCTGTCCT GGAGTTTTCA GAGGGACGCG TATGTGCCAC AGAGCGTC      7620

GCTGGTGGGG GTCATGGGAA GCCATGACCT GGGATAGACA GTCGTCTGTA GAGTGGGG      7680

AACATTCCCT GGGCCCTCTG TTTCATCACT CCTCTTCTCT GTTCCCCCTA CCTCCTGT      7740

ACAGTGGATA CTGAGGCTGT GTGGCTGCTC CAAGGCTGGC TCTTCCAGCA CCAGCCGC      7800

TTCTGGGGGC CCGCCCAGAT CAGGGCTGTG CTGGGAGCTG TGCCCGTGG CCGCCTCC      7860

GTTCTGGACC TGTTTGCTGA GAGCCAGCCT GTGTATACCC GCACTGCCTC CTTCCAGG      7920

CAGCCCTTCA TCTGGTGCAT GCTGCACAAC TTTGGGGGAA ACCATGGTCT TTTTGGAG      7980

CTAGAGGCTG TGAACGGAGG CCCAGAAGCT GCCCGCCTCT TCCCCAACTC CACCATGG      8040

GGCACGGGCA TGGCCCCCGA GGGCATCAGC CAGAACGAAG TGGTCTATTC CCTCATGG      8100
```

```
GAGCTGGGCT GGCGAAAGGA CCCAGTGCCA GATTTGGCAG CCTGGGTGAC CAGCTTTG      8160
GCCCGGCGGT ATGGGGTCTC CCACCCGGAC GCAGGGGCAG CGTGGAGGCT ACTGCTCC      8220
AGTGTGTACA ACTGCTCCGG GGAGGCCTGC AGGGGCCACA ATCGTAGCCC GCTGGTCA      8280
CGGCCGTCCC TACAGATGAA TACCAGCATC TGGTACAACC GATCTGATGT GTTTGAGG      8340
TGGCGGCTGC TGCTCACATC TGCTCCCTCC CTGGCCACCA GCCCCGCCTT CCGCTACG      8400
CTGCTGGACC TCACTCGGCA GGCAGTGCAG GAGCTGGTCA GCTTGTACTA TGAGGAGG      8460
AGAAGCGCCT ACCTGAGCAA GGAGCTGGCC TCCCTGTTGA GGGCTGGAGG CGTCCTGG      8520
TATGAGCTGC TGCCGGCACT GGACGAGGTG CTGGCTAGTG ACAGCCGCTT CTTGCTGG      8580
AGCTGGCTAG AGCAGGCCCG AGCAGCGGCA GTCAGTGAGG CCGAGGCCGA TTTCTACG      8640
CAGAACAGCC GCTACCAGCT GACCTTGTGG GGGCCAGAAG GCAACATCCT GGACTATG      8700
AACAAGCAGC TGGCGGGGTT GGTGGCCAAC TACTACACCC CTCGCTGGCG GCTTTTCC      8760
GAGGCGCTGG TTGACAGTGT GGCCCAGGGC ATCCCTTTCC AACAGCACCA GTTTGACA      8820
AATGTCTTCC AACTGGAGCA GGCCTTCGTT CTCAGCAAGC AGAGGTACCC CAGCCAGC      8880
CGAGGAGACA CTGTGGACCT GGCCAAGAAG ATCTTCCTCA AATATTACCC CGGCTGGG      8940
GCCGGCTCTT GGTGATAGAT TCGCCACCAC TGGGCCTTGT TTTCCGCTAA TTCCAGGG      9000
GATTCCAGGG CCCAGAGCTG ACAGACATC ACAGGATAAC CCAGGCCTGG GAGGAGGC      9060
CACGGCCTGC TGGTGGGGTC TGACCTGGGG GGATTGGAGG GAAATGACCT GCCCTCCA      9120
ACCACCCAAA GTGTGGGATT AAAGTACTGT TTTCTTTCCA CTTAAACTGA TGAGTCCC      9180
GGGTCTGTCA AAATGAGAAG GTCACTGCTG CCACGCTTGG GAGGACTCAG GGCTATAG      9240
TGGCCCTGGG GTGGGACCTG TTCTCCCATC CCTTGCCTCA CGTCCCTGTT TTTGTTTG      9300
TGTTTGTTTG TGACGGAGCC TTGGTCTGTT GCCCAGGCTT GAGTACAATG GCACAGTC      9360
GGCTCACTGC AACCTCCGCC TCCTGGGTTC AAGCAATTCT TGTGCCTCAG CCTCCCCG      9420
AGCTGGGACT ATAGGCATGC ACCACCACAC CAGGCTAATT TTTTTTTTTC CAAGATGG      9480
TCTTGCTCTG TCGCCCAGGT TGGAGTTTAG TGGCACCATA TTGGTTTACT GCAACCTC      9540
CCTCCCGGGT TCAAGCAATT CTCCTGCCTC AGTCTACCAG GGAGTTAGGA CTACGGGC      9600
GTGCCATCAC GCCTGGCTAA TTTTTGTATT TTTCATAGAG ATAAGGTTTC ACCATGTT      9660
CCAGGCTGGT CTTTAACTCC TGAACTCAAG TGATCCACCT GCCTCGGCCT TCCAAAGT      9720
TGGGATTACA GGAGTGAGCC ACCGTGCCCG GCCATGTCTC TCTTTTTAAC ACTAATGT      9780
CCCTGACCTT TGAACGTAGA ATGCCCTTCT GTTGCAGGAA AACCTCTTTT CAAACCAT      9840
TTGTCCTTTG CTGGCATGCC ACAGCAACAG TCACCAACAC AGAAGACTTC TGTGACCA      9900
TATTTGGAGG ATTTTCCCCA CACACACCAA GCAGCAGACA TCAGCTGGGT GTCCTCCA      9960
TCAGTTCCAA TGTAATCAAC CAGAGACAGC ATCAGATCCC ACAGGGTTAG GGTGCAG      10020
CATGAGACCA CCCCCTCCTT CCCAACGGTT ACAAGTCCTG ATCCCTGGAA CTTCTGA      10080
ACTGGCTTCA AGTGGAGTT CCCATGACCC CCTTCCCCTC TTTGGAGTCA ACTCATT      10140
GACAGTGACC CACGAAACAC AGGGAAACCC TTATTATGTT TATTGCTTTA TTACAGA      10200
AAAAAATTTT TTTCTTTCTT TTTTGAGACA GGGTCTCACT CTGTCATCCA GAATGAC      10260
AGTGGCAGGA TCTGGCTCCG TCACCCAGGC TGGAGTGCAG TGGCATGATC TCGGCTC      10320
ACAGCCTCCA TCCCCCCCAA ACCCCACGCC TCAGCGCCCC ACCCCGCAAG TGGCTGG      10380
```

```
(2) INFORMATION FOR SEQ ID NO: 4:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (iii) HYPOTHETICAL: NO (v) FRAGMENT TYPE: N-terminal (vi) ORIGINAL SOURCE:
        (A) ORGANISM: Homo sapiens (ix) FEATURE:
        (A) NAME/KEY: Modified-site
        (B) LOCATION: 10

(xi) SEQUENCE DESCRIPTION: SEQ ID NO: 4:

Asp Glu Ala Arg Glu Ala Ala Ala Val Arg Ala Leu Val Ala Arg
 1               5                  10                  15

Leu Leu Gly Pro Gly
                20

(2) INFORMATION FOR SEQ ID NO: 5:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (iii) HYPOTHETICAL: NO (v) FRAGMENT TYPE: N-terminal (vi) ORIGINAL SOURCE:
        (A) ORGANISM: Homo sapiens (ix) FEATURE:
        (A) NAME/KEY: Modified-site, glycosylated or phosphorylated,
            wherein Xaa may be any amino acid residue, preferably Arg.
        (B) LOCATION: 16

(xi) SEQUENCE DESCRIPTION: SEQ ID NO: 5:

Lys Pro Gly Leu Asp Thr Tyr Ser Leu Gly Gly Gly Gly Ala Ala Xaa Val
 1               5                  10                  15

Arg (2) INFORMATION FOR SEQ ID NO: 6:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Homo sapiens (ix) FEATURE:
        (A) NAME/KEY: Modified-site, glycosylated or phosphorylated,
            wherein Xaa may be any amino acid residue, preferably Ala
        (B) LOCATION: 12
```

```
       (ix) FEATURE:
           (A) NAME/KEY: Modified-site, glycosylated or phosphorylated,
               wherein Xaa may be any amino acid residue, preferably Ser
           (B) LOCATION: 14

(xi) SEQUENCE DESCRIPTION: SEQ ID NO: 6:

Trp Arg Leu Leu Leu Thr Ser Ala Pro Ser Leu Xaa Thr Xaa Pro
1               5                   10                  15
```

SYNTHETIC MAMMALIAN α-N-ACETYLGLUCOSAMINIDASE AND GENETIC SEQUENCES ENCODING SAME

CROSS REFERENCE TO RELATED APPLICATIONS

This application is a continuation application of U.S. Ser. No. 09/836,613, filed Apr. 17, 2001 now abandoned, which is a divisional application of U.S. Ser. No. 09/077,354 now U.S. Pat. No. 6,255,096, which was a section 371 application of PCT/AU96/00747 having an International Filing Date of Nov. 22, 1996.

FIELD OF THE INVENTION

The present invention relates generally to mammalian α-N-acetylglucosaminidase and to genetic sequences encoding same and to the use of these in the investigation, diagnosis and treatment of subjects suspected of or suffering from α-N-acetylglucosaminidase deficiency.

Bibliographic details of the publications referred to by author in this specification are collected at the end of the description. Sequence Identity Numbers (SEQ ID NOs.) for the nucleotide and amino acid sequences referred to in the specification are defined following the bibliography.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

BACKGROUND TO THE INVENTION

The increasing sophistication of recombinant DNA technology is greatly facilitating the efficacy of many commercially important industries including areas of medical and pharmaceutical research and development. The ability to purify native proteins and subsequently clone genetic sequences encoding these proteins is an important first step in the development of a range of therapeutic and diagnostic procedures. However, practitioners have faced many difficulties in purifying target molecules to an extent sufficient to determine amino acid sequences to permit the development of oligonucleotide probes to assist in the cloning of genetic sequences encoding the target molecules.

Such difficulties have been particularly faced in the research and development of lysosomal enzymes. An important lysosomal enzyme is α-N-acetylglucosaminidase (EC 2.1.50). This enzyme acts as a exoglycosidase in lysosomes to hydrolyse the terminal α-N-acetylglucosamine residues present at the non-reducing terminus of fragments of heparan sulphate and heparin (Hopwood, 1989). A deficiency in this lysosomal hydrolase is responsible for the pathogenesis of Sanfilippo B (Mucopolysaccharidosis type IIIB [MPS-IIIB]) syndrome (von-Figura and Kresse, 1972; O'Brien, 1972). This is an autosomal recessive disorder of glycosaminoglycan catabolism leading to storage and excretion of excessive amounts of heparan sulphate and a variety of clinical phenotypes, but classically presenting with progressive mental retardation in conjunction with skeletal deformities (McKusick and Neufeld, 1983).

There is a need, therefore, to purify α-N-acetylglucosaminidase and to clone genetic sequences encoding same to permit development of a range of therapeutic and diagnostic procedures to assist in the diagnosis and treatment of disease conditions arising from α-N-acetylglucosaminidase deficiency.

SUMMARY OF THE INVENTION

One aspect of the invention provides an isolated nucleic acid molecule comprising a sequence of nucleotides which encodes or is complementary to a sequence which encodes a mammalian α-N-acetylglucosaminidase or fragment or derivative thereof.

A second aspect of the invention provides an isolated nucleic acid molecule comprising a sequence of nucleotides which is capable of hybridising under at least low stringency conditions to a nucleotide sequence set forth in SEQ ID NO:1 or SEQ ID NO:3 or a complementary strand or a homologue, analogue or derivative thereof.

Another aspect of the invention is directed an isolated nucleic acid molecule which is at least 40% identical to the nucleotide sequence set forth in SEQ ID NO:1 or SEQ ID NO:3 or to a complementary strand thereof or a homologue, analogue or derivative thereof.

A further aspect of the present invention provides a nucleic acid molecule comprising a sequence of nucleotides encoding or complementary to a sequence encoding a polypeptide capable of hydrolysing the terminal α-N-acetylglucosamine residues present at the non-reducing terminus of fragments of heparan sulphate and heparin residues and wherein said nucleotide sequence is capable of hybridising under low stringency conditions to the nucleotide sequence set forth in SEQ ID NO: 1.

A further aspect of the invention is directed to a genetic construct comprising a sense molecule, for the expression or over-expression of α-N-acetylglucosaminidase in prokaryotic or eukaryotic cells.

A further aspect of the present invention is directed to synthetic α-N-acetylglucosaminidase or like molecule.

A further aspect of the invention contemplates antibodies to α-N-acetylglucosaminidase and preferably synthetic α-N-acetylglucosaminidase or a like molecule.

In still yet another aspect of the present invention there is contemplated a method of diagnosing a mutation or other abberations in the α-N-acetylglucosaminidase gene in a human or animal patient.

Another aspect contemplates a method of treating patients suffering from α-N-acetylglucosaminidase deficiency, such as in MPS-IIIB, said method comprising administering to said patient an effective amount of α-N-acetylglucosaminidase or active like form thereof.

Another aspect of the present invention is directed to a pharmaceutical composition comprising a recombinant mammalian α-N-acetylglucosaminidase or an active fragment or derivative thereof and one or more pharmaceutically acceptable carriers and/or diluents.

Figure 1:
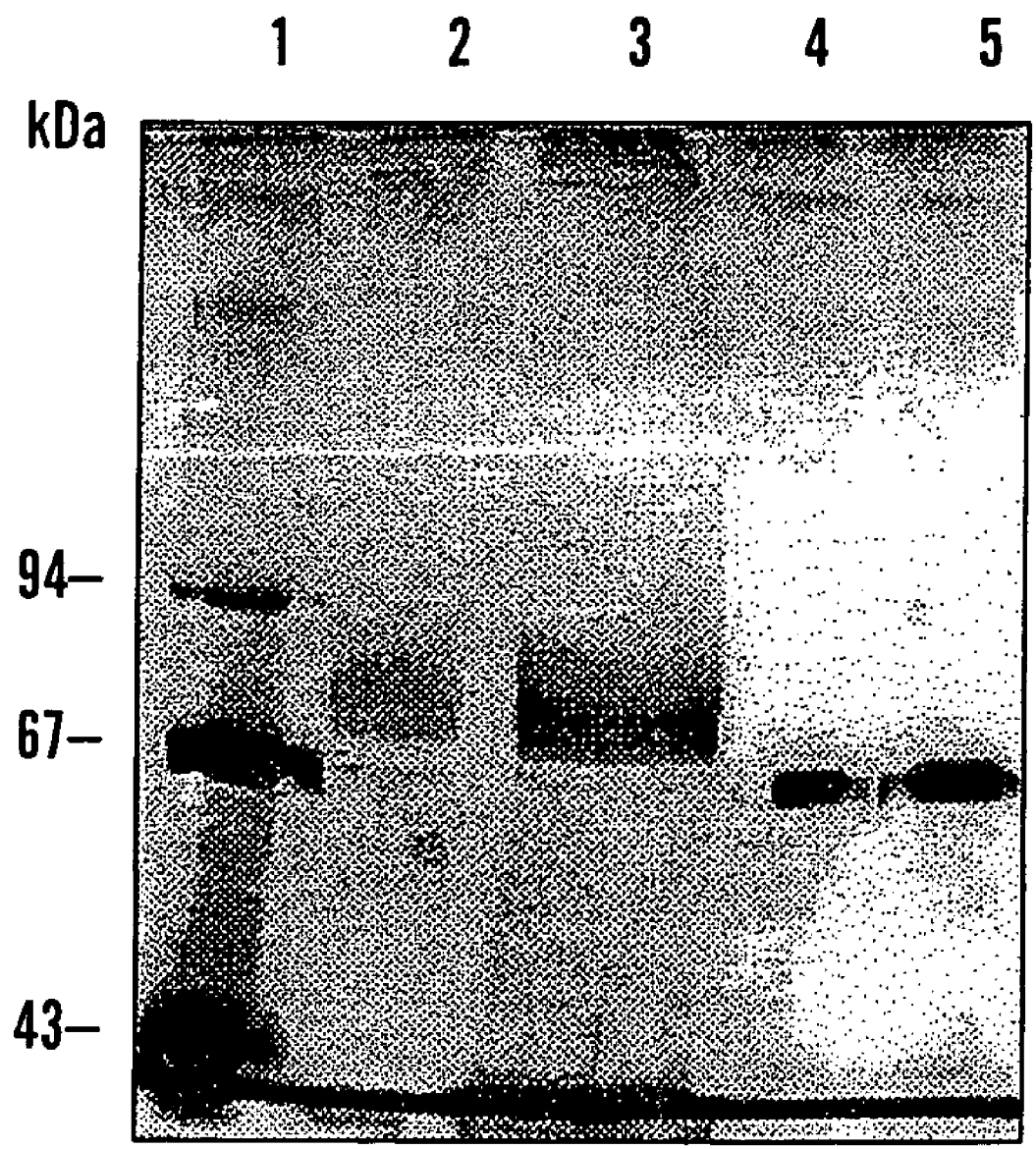
FIG. 1 is a photographic representation of α-N-acetylglucosaminidase purified from human placenta following SDS/PAGE. Lane 1: $M_r$ standards (kDa); Lanes 2 and 3: purified α-N-acetylglucosaminidase from human placenta. Lane 4 and 5, bovine serum albumin.

Molecular weights of α-N-acetylglucosaminidase polypeptides are indicated on the left of the figure. Molecular weights of marker proteins are indicated on the right hand side of the figure (lane 5).

Single and three letter abbreviations of conventional amino acid residues as used herein are defined in Table 1.

Suitable amino acid substitutions referred to herein are defined in Table 2.

Codes for non-conventional amino acid residues as used herein are defined in Table 3.

TABLE 1

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

TABLE 2

Suitable residues for amino acid substitutions

| Original Residue | Exemplary Substitutions |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

TABLE 3

| Non-conventional amino acid | Code |
|---|---|
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |

TABLE 3-continued

| Non-conventional amino acid | Code |
|---|---|
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |

TABLE 3-continued

| Non-conventional amino acid | Code |
|---|---|
| N-(N-(2,2-diphenylethyl) carbamylmethyl)glycine | Nnbhm |
| 1-carboxy-1-(2,2-diphenyl-ethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomo phenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomo phenylalanine | Nmhphe |
| N-(N-(3,3-diphenylpropyl) carbamylmethyl)glycine | Nnbhe |

DETAILED DESCRIPTION OF THE PREFERRED EMBODIMENTS

The present invention provides an isolated nucleic acid molecule comprising a sequence of nucleotides which encodes, or are complementary to a sequence which encodes, a mammalian α-N-acetylglucosaminidase or fragment or derivative thereof or its like molecule.

Preferably, the mammal is a human, livestock animal, companion animal, wild animal or laboratory test animal (e.g. rabbit, rat, mouse or guinea pig). Most preferably, the mammal is a human. Conveniently, the α-N-acetylglucosaminidase is isolatable from the liver, kidney or placenta. However, the present invention extends to all mammalian α-N-acetylglucosaminidase enzymes and from any anatomical or cellular source and/or any biological fluid source, such as but not limited to plasma, serum, cell extract or lymph fluid.

Although a preferred embodiment of the present invention contemplates the use of human α-N-acetylglucosaminidase or genomic or recombinant (e.g. cDNA) genetic sequences encoding same in the investigation, diagnosis and/or treatment of human subjects (i.e. homologous system), one skilled in the art will appreciate that the enzyme or genetic sequences encoding same from a non-human animal may also be useful. Such a heterologous system is encompassed by the present invention.

The term "nucleic acid molecule" as used herein shall be taken to refer to any RNA or DNA (e.g. cDNA) molecule, whether single-stranded or double-stranded or in a linear or covalently-closed form. The nucleic acid molecule may also be DNA corresponding to the entire genomic gene or a substantial portion thereof or a fragment or derivative thereof.

The nucleic acid molecule of the present invention may constitute solely the nucleotide sequence encoding α-N-acetylglucosaminidase or a α-N-acetylglucosaminidase-like molecule or may be part of a larger nucleic acid molecule. Accordingly, the present invention extends to the isolated genomic α-N-acetylglucosaminidase gene. The non-translated sequences in a larger nucleic acid molecule may include vector, transcriptional and/or translational regulatory sequences, promoter, terminator, enhancer, replication or signal sequences or non-coding regions (eg intron sequences) of an isolated genomic gene.

Reference herein to a "gene" is to be taken in its broadest context and includes:

(i) a classical genomic gene consisting of transcriptional and/or translational regulatory sequences and/or a coding region and/or non-translated sequences (i.e. introns, 5'- and 3'-untranslated sequences);

(ii) mRNA or cDNA corresponding to the coding regions (i.e. exons) optionally comprising 5'- or 3'-untranslated sequences of the gene; or (iii) synthetic, amplified DNA fragments or other recombinant nucleic acid molecules produced in vitro and comprising all or a part of the coding region and/or 5'- or 3'-untranslated sequences of the gene.

The term "gene" is also used to describe synthetic or fusion molecules encoding all or part of a functional product. A functional product is one which comprises a sequence of nucleotides or is complementary to a sequence of nucleotides which encodes a functional polypeptide, in particular a polypeptide having the catalytic activity of α-N-acetylglucosaminidase or a homologue, analogue or derivative thereof.

For the present purpose, "homologues" of a nucleotide sequence shall be taken to refer to an isolated nucleic acid molecule which is substantially the same as the nucleic acid molecule of the present invention or its complementary nucleotide sequence, notwithstanding the occurrence within said sequence, of one or more nucleotide substitutions, insertions, deletions, or rearrangements.

"Analogues" of a nucleotide sequence set forth herein shall be taken to refer to an isolated nucleic acid molecule which is substantially the same as a nucleic acid molecule of the present invention or its complementary nucleotide sequence, notwithstanding the occurrence of any non-nucleotide constituents not normally present in said isolated nucleic acid molecule, for example carbohydrates, radiochemicals including radionucleotides, reporter molecules such as, but not limited to DIG, alkaline phosphatase or horseradish peroxidase, amongst others.

"Derivatives" of a nucleotide sequence set forth herein shall be taken to refer to any isolated nucleic acid molecule which contains significant sequence similarity to said sequence or a part thereof. Generally, the nucleotide sequence of the present invention may be subjected to mutagenesis to produce single or multiple nucleotide substitutions, deletions and/or insertions. Nucleotide insertional derivatives of the nucleotide sequence of the present invention include 5' and 3' terminal fusions as well as intra-sequence insertions of single or multiple nucleotides or nucleotide analogues. Insertional nucleotide sequence variants are those in which one or more nucleotides or nucleotide analogues are introduced into a predetermined site in the nucleotide sequence of said sequence, although random insertion is also possible with suitable screening of the resulting product being performed. Deletional variants are characterised by the removal of one or more nucleotides from the nucleotide sequence. Substitutional nucleotide variants are those in which at least one nucleotide in the sequence has been removed and a different nucleotide or nucleotide analogue inserted in its place.

Preferably, a homologue, analogue or derivative of an α-N-acetylglucosaminidase gene according to any embodiments described herein, comprises a sequence of nucleotides of at least 10 contiguous nucleotides derived from SEQ ID NO:1 or SEQ ID NO:3 or a complementary strand thereof, wherein the sequence of said homologue, analogue or derivative is at least 40% identical to SEQ ID NO:1 or SEQ ID NO:3 or a complementary strand thereof or wherein said homologue, analogue or derivative is capable of hybridising to said sequence under at least low stringency hybridisation conditions.

For the purposes of nomenclature, the nucleotide sequence set for in SEQ ID NO: 1 relates to the cDNA encoding the human α-N-acetylglucosaminidase enzyme.

The nucleotide sequence set forth in SEQ ID NO:3 relates to the genomic gene equivalent of the cDNA encoding the human liver α-N-acetylglucosaminidase enzyme. Those skilled in the art will be aware that the specific exon sequences described in SEQ ID NO:3 correspond to the coding regions of the α-N-acetylglucosaminidase gene, said exon regions further comprising the entire open reading frame of the cDNA sequence set forth in SEQ ID NO:1, when aligned in a head-to-tail configuration. The intron sequences of SEQ ID NO:3, which correspond to non-coding regions of the gene which are spliced from the primary transcription product thereof, although not explicitly defined, may be readily deduced by those skilled in the art, when provided with the exon sequence data provided in the nucleotide sequence listing.

The nucleotide sequence of the present invention may correspond to the sequence of the naturally-occurring α-N-acetylglucosaminidase gene or may comprise a homologue, analogue or derivative thereof which contains single or multiple nucleotide substitutions, deletions and/or additions. All such homologues, analogue or derivatives encode α-N-acetylglucosaminidase or α-N-acetylglucosaminidase-like molecules or a homologue, analogue or derivative thereof as contemplated by the present invention. The length of the nucleotide sequence may vary from a few bases, such as in nucleic acid probes or primers, to a full length sequence.

The present invention is particularly directed to the nucleic acid in cDNA form and particularly when inserted into an expression vector. The expression vector may be replicable in a eukaryotic or prokaryotic cell and may either produce mRNA or the mRNA may be subsequently translated into α-N-acetylglucosaminidase or like molecule. Particularly preferred eukaryotic cells include CHO cells but may be in any other suitable mammalian cells or cell lines or non-mammalian cells such as yeast or insect cells.

In an alternative embodiment, the present invention provides a nucleic acid molecule comprising a sequence of nucleotides which encodes or are complementary to a sequence which encodes a polypeptide capable of hydrolysing the α-N-acetylglucosamine residues from the non-reducing terminus of heparan sulphate and heparin fragments and wherein said nucleotide sequence is capable of hybridising under at least low stringency conditions to a nucleotide sequence set forth in SEQ ID NO: 1 or SEQ ID NO:3 or a homologue, analogue or derivative thereof.

A second aspect of the invention provides an isolated nucleic acid molecule comprising a sequence of nucleotides which is capable of hybridising under at least low stringency conditions to a nucleotide sequence set forth in SEQ ID NO:1 or SEQ ID NO:3 or a complementary strand or a homologue, analogue or derivative thereof.

Preferably, hybridisation is possible under at least medium stringent conditions. More preferably, hybridisation is possible under high stringent conditions.

For the purposes of defining the level of stringency, reference can conveniently be made to Sambrook et al (1989) or Ausubel et al (1987) which are herein incorporated by reference.

A low stringency is defined herein as being a hybridisation and/or wash carried out in 4-6×SSC/0.1-0.5% w/v SDS at 37-45° C. for 2-3 hours. A medium stringency hybridisation and/or wash is carried out in 1-4×SSC/0.25-0.5% w/v SDS at ≧45° C. for 2-3 hours and a high stringency hybridisation and/or wash is carried out 0.1-1×SSC/0.1% w/v SDS at 60° C. for 1-3 hours.

Alternative conditions of stringency may be employed to those specifically recited herein. Generally, the stringency is increased by reducing the concentration of SSC buffer, and/or increasing the concentration of SDS and/or increasing the temperature of the hybridisation and/or wash. Those skilled in the art will be aware that the conditions for hybridisation and/or wash may vary depending upon the nature of the hybridisation membrane or the type of hybridisation probe used. Conditions for hybridisations and washes are well understood by one normally skilled in the art. For the purposes of clarification of parameters affecting hybridisation between nucleic acid molecules, reference is found in pages 2.10.8 to 2.10.16. of Ausubel et al. (1987), which is herein incorporated by reference.

Those skilled in the art will be aware that the nucleotide sequences set forth in SEQ ID NO: 1 and SEQ ID NO:3 may be used to isolate the corresponding genes from other human tissues or alternatively, from the tissues or cells of other species, without undue experimentation. Means for the isolated of such related sequences will also be known to those skilled in the art, for example nucleic acid hybridisation, polymerase chain reaction, antibody screening of expression libraries, functional screening of expression libraries, or complementation of mutants, amongst others. The present invention is not to be limited by the source from which the specific gene sequences described herein have been isolated or by the means used to isolate said sequences.

In one embodiment, a related genetic sequence comprising genomic DNA, or mRNA, or cDNA is contacted with a hybridisation effective amount of a genetic sequence which encodes α-N-acetylglucosaminidase, or its complementary nucleotide sequence or a homologue, analogue, derivative or functional part thereof, and then said hybridisation is detected using a suitable detection means.

The related genetic sequence may be in a recombinant form, in a virus particle, bacteriophage particle, yeast cell, animal cell, or a plant cell. Preferably, the related genetic sequence originates from an animal species or a human. More preferably, the related genetic sequence originates from a human.

Preferably, the genetic sequence which encodes α-N-acetylglucosaminidase (i.e. probe or latter genetic sequence) comprises a sequence of nucleotides of at least 10 nucleotides, more preferably at least 20 nucleotides, even more preferably at least 50 nucleotides and even still more preferably at least 100 nucleotides derived from the nucleotide sequence set forth in SEQ ID NO:1 or SEQ ID NO:3 or a complementary sequence or a homologue, analogue or derivative thereof.

Preferably, the detection means is a reporter molecule capable of giving an identifiable signal (e.g. a radioisotope such as $^{32}P$ or $^{35}S$ or a biotinylated molecule) covalently attached to the α-N-acetylglucosaminidase probe.

In an alternative embodiment, the detection means is a polymerase chain reaction. According to this embodiment, two opposing non-complementary nucleic acid "primer molecules" of at least 10 nucleotides in length, more preferably at least 20 nucleotides in length, derived from the nucleotide sequence set forth in SEQ ID NO:1 or SEQ ID NO:3 may be contacted with a nucleic acid "template molecule" and specific nucleic acid molecule copies of the template molecule amplified in a polymerase chain reaction.

The opposing primer molecules are selected such that they are each capable of hybridising to complementary strands of the same template molecule, wherein DNA polymerase-dependant DNA synthesis occurring from a first opposing primer molecule will be in a direction toward the second opposing primer molecule.

Accordingly, both primers hybridise to said template molecule such that, in the presence of a DNA polymerase enzyme, a cofactor and appropriate substrate, DNA synthesis occurs in the 5' to 3' direction from each primer molecule towards the position on the DNA where the other primer molecule is hybridised, thereby amplifying the intervening DNA.

Those skilled in the art are aware of the technical requirements of the polymerase chain reaction and are capable of any modifications which may be made to the reaction conditions. For example, of the polymerase chain reaction may be used in any suitable format, such as amplified fragment length polymorphism (AFLP), single-strand chain polymorphism (SSCP), amplification and mismatch detection (AMD), interspersed repetitive sequence polymerase chain reaction (IRS-PCR), inverse polymerase chain reaction (iPCR) and reverse transcription polymerase chain reaction (RT-PCR), amongst others, to isolate a related α-N-acetylglucosaminidase gene sequence or identify a mutation in an α-N-acetylglucosaminidase genetic sequence. Such variations of the polymerase chain reaction are discussed in detail by McPherson et al (1991), which is incorporated herein by reference. The present invention encompasses all such variations, the only requirement being that the final product of the reaction is an isolated nucleic acid molecule which is capable of encoding α-N-acetylglucosaminidase or a homologue, analogue or derivative thereof.

In a preferred embodiment, the first primer molecule is preferably derived from the sense strand of a gene which encodes α-N-acetylglucosaminidase, in particular from the nucleotide sequence set forth in SEQ ID NO: 1 or SEQ ID NO:3 or a homologue, derivative or analogue thereof and the second primer molecule is preferably derived from the antisense strand of said gene.

Those skilled in the art will be aware that it is not essential to the performance of the invention that the primer molecules be derived from the same gene.

According to this embodiment, the nucleic acid primer molecule may further consist of a combination of any of the nucleotides adenine, cytidine, guanine, thymidine, or inosine, or functional analogues or derivatives thereof, capable of being incorporated into a polynucleotide molecule provided that it is capable of hybridising under at least low stringency conditions to the nucleic acid molecule set forth in SEQ ID NO:1 or SEQ ID NO:3 or a homologue, analogue or derivative thereof.

The nucleic acid primer molecules may further be each contained in an aqueous pool comprising other nucleic acid primer molecules. More preferably, the nucleic acid primer molecule is in a substantially pure form.

The nucleic acid template molecule may be in a recombinant form, in a virus particle, bacteriophage particle, yeast cell, animal cell, or a plant cell. Preferably, the related genetic sequence originates from a cell, tissue, or organ derived from an animal species or a human. More preferably, the related genetic sequence originates from a cell, tissue, or organ derived from a human.

Accordingly, a third aspect of the present invention extends to an isolated nucleic acid molecule which is at least 40% identical to the nucleotide sequence set forth in SEQ ID NO:1 or SEQ ID NO:3 or to a complementary strand thereof or a homologue, analogue or derivative thereof.

Preferably, the percentage identity to SEQ ID NO:1 or SEQ ID NO:3 is at least about 55%, still more preferably at least about 65%, yet still more preferably at least about 75-80% and even still more preferably at least about 85-95%.

In an even more preferred embodiment, the present invention provides an isolated nucleic acid molecule which is at least 40% identical to the nucleotide sequence set forth in SEQ ID NO:1 or SEQ ID NO:3 or to a complementary strand thereof or a homologue, analogue or derivative thereof and is capable of hybridising under at least low stringency conditions to a nucleotide sequence set forth in SEQ ID NO:1 or SEQ ID NO:3.

In a particularly preferred embodiment, the isolated nucleic acid molecule described herein is further capable of encoding a sequence of amino acids which is capable of carrying out the enzyme reaction catalysed by a α-N-acetylglucosaminidase enzyme.

The isolated nucleic acid molecule of the present invention is also useful for developing a genetic construct comprising a sense molecule, for the expression or over-expression of α-N-acetylglucosaminidase in prokaryotic or eukaryotic cells. Particularly preferred eukaryotic cells include CHO cells but may be in any other suitable mammalian cells or cell lines or non-mammalian cells such as yeast or insect cells.

The term "sense molecule" as used herein shall be taken to refer to an isolated nucleic acid molecule of the invention as described herein, which is provided in a format suitable for its expression to produce a recombinant polypeptide, when said sense molecule is introduced into a host cell.

In a particularly preferred embodiment, a sense molecule which encodes the α-N-acetylglucosaminidase comprises a sequence of nucleotides set forth in SEQ ID NO:1 or SEQ ID NO:3 or a complementary strand, homologue, analogue or derivative thereof.

In a most particularly preferred embodiment, the sense molecule of the invention comprises the sequence of nucleotides set forth in SEQ ID NO:1 or a complementary strand, homologue, analogue or derivative thereof.

Those skilled in the art will be aware that expression of a sense molecule may require the nucleic acid molecule of the invention to be placed in operable connection with a promoter sequence to produce a "sense construct". The choice of promoter for the present purpose may vary depending upon the level of expression of the sense molecule required and/or the tissue-specificity or developmental-specificity of expression of the sense molecule which is required. The sense construct may further comprise a terminator sequence and be introduced into a suitable host cell where it is capable of being expressed to produce a recombinant polypeptide gene product.

In the context of the present invention, a sense molecule which corresponds to a genetic sequence or isolated nucleic acid molecule which encodes α-N-acetylglucosaminidase polypeptide or a homologue, analogue or derivative thereof, placed operably under the control of a suitable promoter sequence, is introduced into a cell using any suitable method for the transformation of said cell and said genetic sequence or isolated nucleic acid molecule is expressed therein to produce said polypeptide.

The present invention clearly extends to genetic constructs designed to facilitate expression of any nucleic acid molecule described herein.

A genetic construct of the present invention comprises the foregoing sense molecule, placed operably under the control of a promoter sequence capable of regulating the expression of the said nucleic acid molecule in a prokaryotic or eukaryotic cell, preferably a mammalian cell such as a CHO cell, a yeast cell, insect cell or bacterial cell. The said genetic construct optionally comprises, in addition to a promoter and sense molecule, a terminator sequence.

The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in plant cells are known and described in the literature. They may be isolated from bacteria, fungi, viruses, animals and/or plants.

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or external stimuli, or in a tissue-specific manner. A promoter is usually, but not necessarily, positioned upstream or 5', of a structural gene, the expression of which it regulates. Furthermore, the regulatory elements comprising a promoter are usually positioned within 2 kb of the start site of transcription of the gene.

In the present context, the term "promoter" is also used to describe a synthetic or fusion molecule, or derivative which confers, activates or enhances expression of said sense molecule in a cell.

Preferred promoters may contain additional copies of one or more specific regulatory elements, to further enhance expression of the sense molecule and/or to alter the spatial expression and/or temporal expression of said sense molecule. For example, regulatory elements which confer copper inducibility may be placed adjacent to a heterologous promoter sequence driving expression of a sense molecule, thereby conferring copper inducibility on the expression of said molecule.

Placing a sense molecule under the regulatory control of a promoter sequence means positioning the said molecule such that expression is controlled by the promoter sequence. Promoters are generally positioned 5' (upstream) to the genes that they control. In the construction of heterologous promoter/structural gene combinations it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art, some variation in this distance can also occur.

Examples of promoters suitable for use in genetic constructs of the present invention include viral, fungal, bacterial, animal and plant derived promoters capable of functioning in animal, human, yeast, insect or bacterial cells. The promoter may regulate the expression of the said molecule constitutively, or differentially with respect to the tissue in which expression occurs or, with respect to the developmental stage at which expression occurs, or in response to external stimuli such as physiological stresses, or plant pathogens, or metal ions, amongst others. Preferably, the promoter is capable of regulating expression of a sense molecule in a cell derived from an animal species or human.

In a particularly preferred embodiment, the promoter is derived from the genomic gene encoding α-N-acetylglucosaminidase, preferably the human α-N-acetylglucosaminidase gene. In a more preferred embodiment, however, the promoter is derived from the nucleotide sequence set forth in SEQ ID NO:3 or is at least capable of hybridising to nucleotide residues 1 to 989 of SEQ ID NO:3 or at least 20 contiguous nucleotides derived therefrom.

In an even more particularly preferred embodiment, the promoter is the CMV promoter sequence or a promoter sequence derived therefrom.

An alternative embodiment of the invention is directed to a genetic construct comprising a promoter or functional derivative, part fragment, homologue, or analogue thereof, derived from the α-N-acetylglucosaminidase genomic gene defined by SEQ ID NO:3.

Preferably, said genetic construct further comprises the α-N-acetylglucosaminidase sequence defined by SEQ ID NO:1 placed in operably connection with said promoter.

A further aspect of the present invention is directed to synthetic α-N-acetylglucosaminidase or like molecule.

The term "synthetic" as used herein shall be taken to include both recombinant and chemically-synthesised molecules produced by the sequential addition of amino acid residues or groups of amino acid residues in defined order.

In one embodiment, the invention relates to recombinant α-N-acetylglucosaminidase or like molecule encoded by or expressed from the nucleic acid molecules as hereinbefore described.

In another embodiment, the synthetic α-N-acetylglucosaminidase or like molecule comprises a sequence of amino acids which is at least 40% identical to the amino acid sequence set forth in any one of SEQ ID Nos:2, 4, 5 or 6.

More preferably, the percentage identity is at least 60% and still more preferably at least 80% or 85-90%.

A particularly preferred embodiment of the present invention provides a synthetic α-N-acetylglucosaminidase as hereinbefore defined which comprises a sequence of amino acids substantially as set forth in any one of SEQ ID Nos:2, 4, 5 or 6 or a homologue, analogue or derivative thereof.

For the purposes of nomenclature, the amino acid sequence set forth in SEQ ID NO:2 comprises the full-length translation product of the human α-N-acetylglucosaminidase gene (i.e. hereinafter referred to as the "α-N-acetylglucosaminidase polypeptide" or "SEQ ID NO:2") produced by expression of either the cDNA sequence defined by SEQ ID NO:1 or the genomic gene defined by SEQ ID NO:3. The α-N-acetylglucosaminidase polypeptide comprises at least seven potentially-glycosylated Asn residues, at positions 261, 272, 435, 503, 513, 526 and 532. Furthermore, the amino acid sequence of the α-N-acetylglucosaminidase polypeptide may comprise a signal peptide of approximately 23 amino acid residues in length, with a probable site for signal peptide peptidase cleavage occurring between $Gly_{23}$ and $Asp_{24}$.

The amino acid sequences set forth in SEQ ID Nos:4-6 relate to N-terminal and internal (i.e. CNBr) amino acid sequences derived from human α-N-acetylglucosaminidase, purified as described in Example 1. As described in Example 2, the purified form of the enzyme comprises two polypeptides having approximate molecular weights of 82 and 77 kDa. The sequence set forth in SEQ ID NO:4 relates to the N-terminal sequence of the 82 kDa polypeptide, while SEQ ID NO:5 relates to the N-terminal sequence of the 77% kDa polypeptide. Furthermore, SEQ ID NO:4 comprises amino acids residues 24-43 of SEQ ID NO:2, while SEQ ID NO:5 comprises amino acid residues 59-76 of SEQ ID NO:2.

The amino acid sequence defined by SEQ ID NO:6 relates to the CNBr-cleaved peptide of purified human α-N-acetylglucosaminidase. This amino acid sequence aligns with amino acid residues 540-554 of the α-N-acetylglucosaminidase polypeptide (SEQ ID NO:2).

In the present context, "homologues" of a polypeptide refer to those polypeptides, enzymes or proteins which have a similar α-N-acetylglucosaminidase enzyme activity, notwithstanding any amino acid substitutions, additions or deletions thereto. A homologue may be isolated or derived from the same or another animal species.

Furthermore, the amino acids of a homologous polypeptide may be replaced by other amino acids having similar properties, for example hydrophobicity, hydrophilicity, hydrophobic moment, charge or antigenicity, and so on.

"Analogues" encompass α-N-acetylglucosaminidase polypeptides and peptide derivatives thereof notwithstanding the occurrence of any non-naturally occurring amino acid analogues therein.

The term "derivative" in relation to the polypeptides of the invention refer to mutants, parts or fragments of a functional molecule. Derivatives include modified peptides in which ligands are attached to one or more of the amino acid residues contained therein, such as carbohydrates, enzymes, proteins, polypeptides or reporter molecules such as radionuclides or fluorescent compounds. Glycosylated, fluorescent, acylated or alkylated forms of the subject peptides are particularly contemplated by the present invention. Additionally, derivatives of a polypeptide may comprise fragments or parts of an amino acid sequence disclosed herein and are within the scope of the invention, as are homopolymers or heteropolymers comprising two or more copies of the subject polypeptides. Procedures for derivatizing peptides are well-known in the art.

Accordingly, this aspect of the present invention is directed to any proteinaceous molecule comprising an amino acid sequence corresponding to the full length mammalian α-N-acetylglucosaminidase enzyme or to a like molecule. The like molecule, therefore, comprises parts, derivatives and/or portions of the α-N-acetylglucosaminidase enzyme whether functional or not.

Preferably, the mammal is human but may be of non-human origin as contemplated above.

The synthetic or recombinant α-N-acetylglucosaminidase of the present invention may comprise an amino acid sequence corresponding to the naturally occurring amino acid sequence or may contain single or multiple amino acid substitutions, deletions and/or additions. The length of the amino acid sequence may range from a few residues to a full length molecule.

Amino acid substitutions are typically of single residues. Amino acid insertions will usually be in the order of about 1-10 amino acid residues and deletions will range from about 1-20 residues. Preferably, deletions or insertions are made in adjacent pairs, i.e. a deletion of two residues or insertion of two residues.

Amino acid insertional derivatives of α-N-acetylglucosaminidase of the present invention include amino and/or carboxyl terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in the sequence has been removed and a different residue inserted in its place. Typical substitutions are those made in accordance with the following Table 2:

The amino acid variants referred to above may readily be made using peptide synthetic techniques well known in the art, such as solid phase peptide synthesis (Merrifield synthesis) and the like, or by recombinant DNA manipulations. Techniques for making substitution mutations at predetermined sites in DNA having known or partially known sequence are well known and include, for example, M13 mutagenesis. The manipulation of DNA sequence to produce variant proteins which manifest as substitutional, insertional or deletional variants are conveniently elsewhere described such as Sambrook et al, 1989 *Molecular Cloning: A Laboratory Manual* Cold Spring Harbor Laboratories, Cold Spring Harbor, N.Y.

The derivatives or like molecules include single or multiple substitutions, deletions and/or additions of any component(s) naturally or artificially associated with the α-N-acetylglucosaminidase enzyme such as carbohydrate, lipid and/or other proteinaceous moieties. For example, the present invention extends to glycosylated and non-glycosylated forms of the molecule. All such molecules are encompassed by the expression "mutants", "derivatives", "fragments", "portions" and "like" molecules. These molecules may be active or non-active and may contain specific regions, such as a catalytic region. Particularly, preferred derivative molecules include those with altered glycosylation patterns relative to the naturally occurring molecule. Even more particularly, the recombinant molecule is more highly glycosylated than the naturally occurring molecule. Such highly glycosylated derivatives may have improved take-up properties and enhanced half-lives.

As indicated in the Examples, the molecular weight of purified human α-N-acetylglucosaminidase (i.e. 82 kDa and 77 kDa) and recombinant mammalian α-N-acetylglucosaminidase produced in CHO cells (i.e. 89 kDa and 79 kDa) are greater than the deduced molecular weight of the α-N-acetylglucosaminidase polypeptide set forth in SEQ ID No:2 (i.e. 70 kDa), suggesting that the purified and recombinant polypeptide are post-translationally modified. The data presented in Example 8 indicate further that the recombinant α-N-acetylglucosaminidase enzyme produced in CHO cells, at least, is glycosylated and that the difference in molecular weight determined for the recombinant polypeptides and the polypeptide of SEQ ID No:2 is due almost entirely to glycosylation of the recombinant polypeptide by CHO cells. As shown in Example 9, the glycosylated recombinant α-N-acetylglucosaminidase polypeptide exhibits enzymatic activity.

The present invention also extends to synthetic α-N-acetylglucosaminidase or like molecules when fused to other proteinaceous molecules. The latter may include another enzyme, reporter molecule, purification site or an amino acid sequence which facilitates transport of the molecule out of a cell, such as a signal sequence.

The present invention extends further to post-translational modifications to the α-N-acetylglucosaminidase enzyme. The modifications may be made to the naturally occurring enzyme or following synthesis by recombinant techniques. The modifications may be at the structural level or at, for example, the electrochemical level such as modifying net charge or structural conformation of the enzyme.

Such modification may be important to facilitate entry or penetration of the enzyme into selected tissues such as cartilage or blood brain barriers or to increase circulation half-life.

Analogues of α-N-acetylglucosaminidase contemplated herein include, but are not limited to, modifications to side chains, incorporation of unnatural amino acids and/or their derivatives during peptide synthesis and the use of crosslinkers and other methods which impose conformational constraints on the enzyme.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5'-phosphate followed by reduction with $NaBH_4$.

The guanidino group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivatisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuric-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. Non-naturally occurring amino acids contemplated by the present invention are incorporated herein, as Table 3.

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, the enzyme could be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

Electrochemical modifications of α-N-acetylglucosaminidase include interaction with polylysine or polyethylene glycol or other agent which effects an overall change to the net charge of the enzyme.

Advantageously, the recombinant α-N-acetylglucosaminidase is a biologically pure preparation meaning that it has undergone some purification away for other proteins and/or non-proteinaceous material. The purity of the preparation may be represented as at least 40% of the enzyme, preferably at least 60%, more preferably at least 75%, even more preferably at least 85% and still more preferably at least 95% relative to non-α-N-acetylglucosaminidase material as determined by weight, activity, amino acid homology or similarity, antibody reactivity or other convenient means.

Particularly preferred methods for the preparation and purification of recombinant α-N-acetylglucosaminidase are provided in Examples 7 and 8.

Those skilled in the art will be aware of the means of purifying a synthetic or recombinant α-N-acetylglucosaminidase from several sources without undue experimentation and for expressing the degree of purity of such a purified preparation of the enzyme.

The present invention further contemplates antibodies to α-N-acetylglucosaminidase and preferably synthetic α-N-acetylglucosaminidase or like molecule. The antibodies may be polyclonal or monoclonal, naturally occurring or synthetic (including recombinant, fragment or fusion forms). Such antibodies will be useful in developing immunoassays for α-N-acetylglucosaminidase and for identifying additional genetic sequences which are capable of expressing α-N-acetylglucosaminidase polypeptides or homologues, analogues or derivatives thereof.

Both polyclonal and monoclonal antibodies are obtainable by immunisation with an appropriate synthetic or recombinant gene product, or epitope, or peptide fragment of a gene product, in particular a α-N-acetylglucosaminidase polypeptide or a homologue, analogue or derivative thereof.

Alternatively, fragments of antibodies may be used, such as Fab fragments. The present invention extends further to encompass recombinant and synthetic antibodies and to antibody hybrids. A "synthetic antibody" is considered herein to include fragments and hybrids of antibodies.

A further aspect of the present invention contemplates a method of screening for mutations or other abberations in the α-N-acetylglucosaminidase gene in a human or animal patient. Such a method may be accomplished in a number of ways including isolating a source of DNA to be tested or mRNA therefrom and hybridising thereto a nucleic acid molecule as hereinbefore described. Generally, the nucleic acid is probe or primer size and polymerase chain reaction is a convenient means by which to analyse the RNA or DNA. Other suitable assays include the ligation chain reaction and the strand displacement amplification methods. The α-N-acetylglucosaminidase sequence can also be determined and compared to the naturally occurring sequence. Such methods may be useful in adults and children and may be adapted for a pre-natal test. The DNA to be tested includes a genomic sample carrying the α-N-acetylglucosaminidase gene, a cDNA clone and/or amplification product.

In accordance with this aspect of the present invention there is provided a method for screening for abberations in the α-N-acetylglucosaminidase gene including the absence of such a gene or a portion or a substantial portion thereof comprising isolating a sample of DNA or mRNA corresponding to a region of said DNA and contacting same with an oligonucleotide probe capable of hybridising to one or more complementary sequences within the α-N-acetylglucosaminidase gene and then detecting the hybridisation, the extent of hybridisation or the absence of hybridisation.

Alternatively, the probe is a primer and capable of directing amplification of one or more regions of said α-N-acetylglucosaminidase gene and the amplification products and/or profile of amplification products is compared to an individual carrying the full gene or to a reference date base.

Conveniently, the amplification products are sequenced to determine the presence or absence of the full gene.

The present invention extends to the use of any and all DNA-based or nucleic acid-based hybridisation and/or polymerase chain reaction formats as described herein, for the diagnosis of a disorder involving the α-N-acetylglucosaminidase gene in a human or animal patient.

The present invention further extends to a method of treating patients suffering from α-N-acetylglucosaminidase deficiency, such as in MPS-IIIB, said method comprising administering to said patient an effective amount of α-N-acetylglucosaminidase or active like form thereof.

Preferably, the α-N-acetylglucosaminidase is in recombinant form. Such a method is referred to as "enzyme therapy". Alternatively, gene therapy can be employed including introducing an active gene (i.e. a nucleic acid molecule as hereinbefore described) or to parts of the gene or other sequences which facilitate expression of a naturally occurring α-N-acetylglucosaminidase gene.

Administration of α-N-acetylglucosaminidase for enzyme therapy may be by oral, intravenous, suppository, intraperitoneal, intramuscular, intranasal, intradermal or subcutaneous administration or by infusion or implantation. The α-N-acetylglucosaminidase is preferably as hereinbefore described including active mutants or derivatives thereof and glycosylation variants thereof. Administration may also be by way of gene therapy including expression of the gene by inclusion of the gene in viral vectors which are introduced into the animal (e.g. human) host to be treated. Alternatively, the gene may be expressed in a bacterial host which is then introduced and becomes part of the bacterial flora in the animal to be tested.

Still yet another aspect of the present invention is directed to a pharmaceutical composition comprising synthetic (e.g. recombinant) α-N-acetylglucosaminidase or like molecule, including active derivatives and fragments thereof, alone or in combination with other active molecules. Such other molecules may act synergistically with the enzyme or facilitates its entry to a target cell. The composition will also contain one or more pharmaceutically acceptable carriers and/or diluents. The composition may alternatively comprise a genetic component useful in gene therapy.

The active ingredients of the pharmaceutical composition comprising the synthetic or recombinant α-N-acetylglucosaminidase or mutants or fragments or derivatives thereof are contemplated to exhibit excellent activity in treating patients with a deficiency in the enzyme when administered in an amount which depends on the particular case. The variation depends, for example, on the patient and the α-N-acetylglucosaminidase used. For example, from about 0.5 ug to about 20 mg of enzyme per animal body or, depending on the animal and other factors, per kilogram of body weight may be administered. Dosage regima may be adjusted to provide the optimum therapeutic response. For example, several divided doses may be administered daily, weekly, monthly or in other suitable time intervals or the dose may be proportionally reduced as indicated by the exigencies of the situation. Accordingly, alternative dosages in the order of 1.0 µg to 15 mg, 2.0 µg to 10 mg or 10 µg to 5 mg may be administered in a single or as part of multiple doses. The active compound may be administered in a convenient manner such as by the oral, intravenous (where water soluble), intramuscular, subcutaneous, intranasal, intradermal or suppository routes or implanting (eg using slow release molecules). Depending on the route of administration, the active ingredients which comprise a synthetic (e.g. recombinant) α-N-acetylglucosaminidase or fragments, derivatives or mutants thereof may be required to be coated in a material to protect same from the action of enzymes, acids and other natural conditions which may inactivate said ingredients. For example, the low lipophilicity of α-N-acetylglucosaminidase will allow it to be destroyed in the gastrointestinal tract by enzymes capable of cleaving peptide bonds and in the stomach by acid hydrolysis. In order to administer the vaccine by other than parenteral administration, the enzyme will be coated by, or administered with, a material to prevent its inactivation. For example, the enzyme may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Conveniently, the adjuvant is Freund's Complete or Incomplete Adjuvant. Enzyme inhibitors include pancreatic trypsin inhibitor, diisopropylfluorophosphate (DEP) and trasylol. Liposomes include water-in-oil-in-water emulsions as well as conventional liposomes.

The active compound may also be administered in dispersions prepared in glycerol, liquid polyethylene glycols, and/or mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, parabens, chlorobutanol, phenol, sorbic acid, thirmerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient(s) into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the α-N-acetylglucosaminidase of the present invention is suitably protected as described above, the composition may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in the vaccine compositions is such that a suitable dosage will be obtained. Preferred compositions or preparations according to the present invention are prepared, so that an oral dosage unit form contains between about 0.5 ug and 20 mg of active compound.

The tablets, troches, pills, capsules and the like may also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavoring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release reparations and formulations.

As used herein "pharmaceutically acceptable carriers and/or diluents" include any and all solvents, dispersion media, aqueous solutions, coatings, antibacterial and antifungal agents, isotonic and absorption delaying agents, and the like. The use of such media and agents for pharmaceutical active substances is well known in the art. Except insofar as any conventional media or agent is incompatible with the active ingredient, use thereof in the pharmaceutical compositions is contemplated. Supplementary active ingredients can also be incorporated into the compositions.

The present invention further relates to the use of α-N-acetylglucosaminidase or active fragment, mutant or derivative thereof in the manufacture of a medicament for the treatment of patients suffering from a deficiency in the naturally occurring enzyme (e.g. MPS-IIIB).

The present invention is further described with reference to the following non-limiting Examples.

EXAMPLE 1

Purification of α-N-Acetylglucosaminidase

α-N-acetylglucosaminidase was purified according to the method described in Weber et al. (1996). Enzyme was purified to homogeneity from human placenta. Evidence of purity is shown following SDS/PAGE which is represented in FIG. 1. All samples were reduced with dithiothreitol prior to electrophoresis.

EXAMPLE 2

Characterisation of α-N-Acetylglucosaminidase

Results presented in FIG. 1 show two polypeptides of about 82 kDa and 77% kDa molecular weight, which correspond to α-N-acetylglucosaminidase polypeptides purified from human placenta according to Example 1.

EXAMPLE 3

Amino Acid Sequence Determination

The N-terminal amino acid sequences the 77% kDA and 82 kDa α-N-acetylglucosaminidase polypeptides, in addition to the amino acid sequence of an internal CNBr cleavage product of these peptides, were determined using the methods of Weber et al. (1996).

The amino acid sequences are shown in Table 4.

TABLE 4

N-Terminal amino acid sequences (SEQ ID NO:4 and SEQ ID No:5) and CNBr peptide sequence (SEQ ID No:6) determined from purified human α-N-Acetylglucosaminidase

| | |
|---|---|
| polypeptide 82 kDa | DEAREAAAVRALVARLLGPG |
| polypeptide 77 kDa | KPGLDTYSLGGGGAAX$^1$ VR |
| CNBr peptide | WRLLLTSAPSLX$^1$ TX$^1$P |

$X^1$ no residue could be identified for this position, indicating that this residue could be phosphorylated or-glycosylated.

EXAMPLE 4

Cloning of α-N-Acetylglucosaminidase cDNA

Oligonucleotide probes were prepared based on the partial amino acid sequences obtained for the purified α-N-acetylglucosaminidase polypeptides (Example 3). The probes were subsequently used to screen a human peripheral blood leukocyte cDNA library. An approximately 2.6 kbp cDNA clone was isolated encoding most of the sequence of human α-N-acetylglucosaminidase (SEQ ID NO:1).

The remaining α-N-acetylglucosaminidase coding sequence was obtained from the nucleotide sequence of the corresponding genomic gene (SEQ ID NO:3), isolated by hybridisation to a human chromosome 17 library (Weber et. al. 1996).

The complete open reading frame is 2232 nucleotides long and encodes a 743 (plus stop codon) amino acid protein. The predicted molecular mass of the longest mature protein (minus the 23 amino acid N-terminal signal peptide) is about 79,622 daltons.

The amino acid sequence of α-N-acetylglucosaminidase is shown in SEQ ID NO:2. The deduced molecular weight of the desired amino acid sequence of α-N-acetylglucosaminidase is approximately 70 kDa. The probable site of signal peptide peptidase cleavage is between amino acids 23 and 24. There are seven potential N-glycosylation sites in the sequence.

The nucleotide sequence of the corresponding α-N-acetylglucosaminidase genomic gene (SEQ ID No:3) comprises 10380 bp including 889 bp of 5' upstream sequence corresponding to at least at part of the α-N-acetylglucosaminidase promoter sequence, in addition to the nucleotide sequences of introns I, II, II, IV, V, in addition to 1326 bp of 3'-untranslated sequence.

EXAMPLE 5

Construction of an Expression Vector Comprising the α-N-Acetylglucosaminidase cDNA Sequence The cDNA insert of λ clone pbl 33, containing bases 107 to 2575 of the α-N-acetylglucosaminidase cDNA was excised with EcoRI and subcloned into pBluescript II SK-(Stratagene). A 178 bp XmaI fragment (bases 1 to 178 of the α-N-acetylglucosaminidase cDNA) from cosmid sub-clone 6.3, containing the start codon, was cloned into the pBluescript subclone to produce a full-length cDNA sequence in addition to 101 bp of 5' non-translated sequence as well as 245 bp of 3' non-translated region including the polyadenylation-site, the poly A-tail and linkerDNA. The full length cDNA was directionally cloned into the pCDNA3 expressionvector (Invitrogen) via the EcoRI and BamHI sites.

EXAMPLE 6

Expression of Recombinant α-N-acetylglucosaminidase

Chinese Hamster Ovary (CHO) cells were transfected with expressionvector using the DOTAP transfection reagent (Boehringer Mannheim) according to the manufacturers instructions. Cells were grown in Ham's F12 medium, 10% (v/v) fetal calf serum, penicillin and streptomycin sulfate at 100 µg/ml each. Cells were grown in nonselective medium for 48 h and then incubated in medium containing 750 µg/ml G418 sulfate (Geniticin) until resistant colonies emerged.

Single cell clones were grown up and 26 of them were tested for expression of recombinant α-N-acetylglucosaminidase with a fluorogenic α-N-acetylglucosaminidase substrate. (i.e. N-acetylglucosamine α-linked to 4-methylumbelliferone)

EXAMPLE 7

Large Scale α-N-acetylglucosaminidase Production 2 g of Cytodex 2 microcarrier beads were swollen in 250 ml of PBS for 3 h at 37° C. with three changes of PBS and then autoclaved for 15 min at 120° C. (wet cycle). The beads were then rinsed with sterile growth medium (Coons/DMEM, 10% v/v fetal calf serum, penicillin and streptomycin sulfate at 100 µg/ml each and 0.1% w/v Pluronic F68) and transferred into a Techne stirrer culture flask. The microcarrier beads were inoculated with seven confluent 175 flasks of the cell clone showing the highest expression of recombinant α-N-acetylglucosaminidase. Growth medium was added up to 200 ml and the culture incubated with a stirrer speed of 20 rpm to achieve an even distribution of cells on the beads. The cells were allowed to attach to the beads for 16 h at low speed then medium was added up to 500 ml and the stirrer speed increased to 30 rpm. After a growth phase of 48 to 72 h with daily aerating to allow gas exchange the beads were completely covered with cells and the medium was exchanged for production medium (Coons/DMEM, no fetal calf serum, penicillin and streptomycin sulfate at 100 µg/ml each, 0.1% w/v Pluronic F68 and 5 mM NH$_4$Cl). The glucose concentration was monitored daily and the medium replaced, when glucose fell below 5 mM every 203 days. The harvested medium contained approximately 2 mg α-N-acetylglucosaminidase protein per dm$^3$ of production medium.

EXAMPLE 8

Purification of Recombinant α-N-acetylglucosaminidase

Production medium was dialysed against 50 mM NaAc pH 5.5 and loaded onto a heparin-agarose column equilibrated in the same buffer. After washing with NaAc buffer and NaAc/ 50 mM NaCl the column was eluted with 75 mM NaCl in NaAc buffer. The eluate was dialysed against 20 mM Tris/ HCl pH 7.5, loaded onto a DEAE Scphacel column, washed with 25 mM NaCl in 20 mM Tris/HCl and then eluted with 50 and 75 mM NaCl in 20 mM Tris/HCl respectively.

Figure 2:
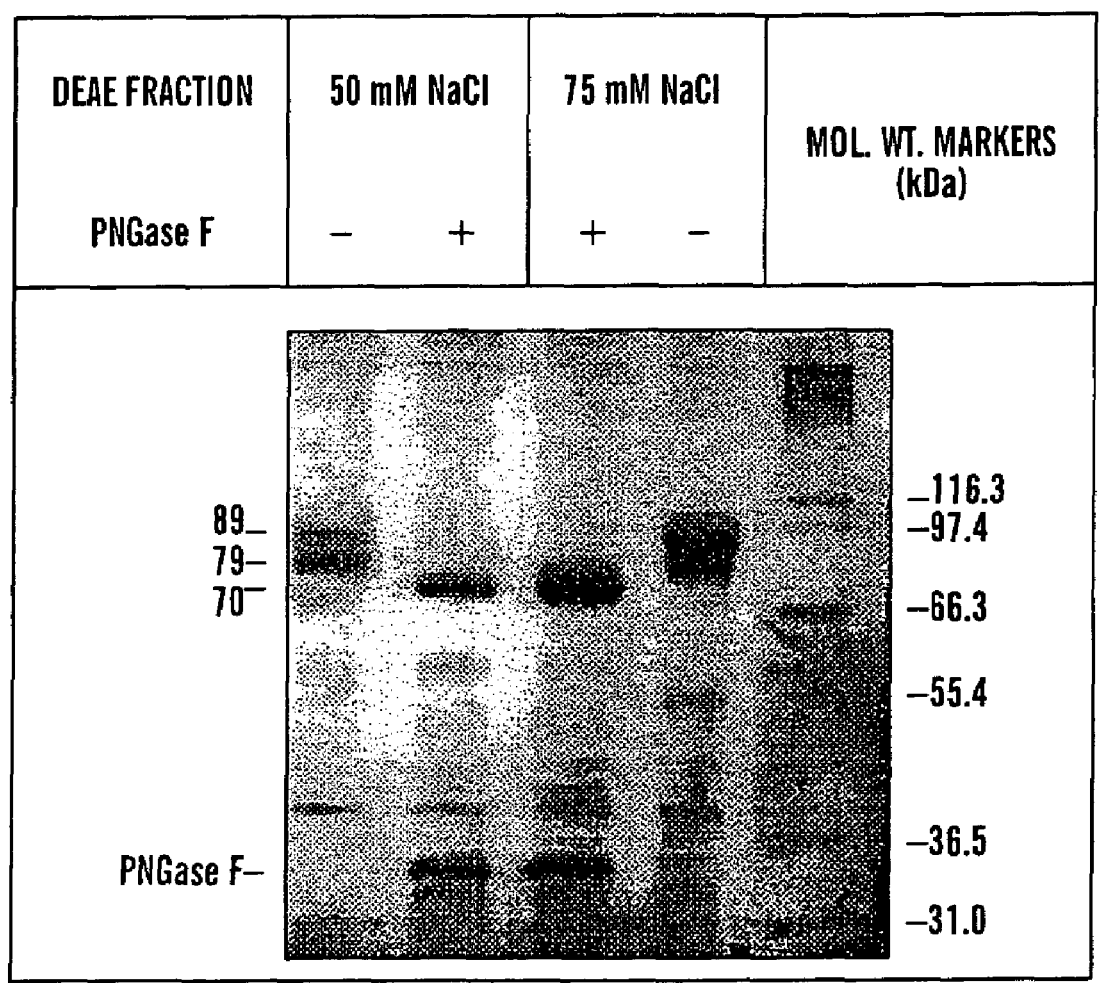
FIG. 2 is a photographic representation of an SDS/polyacrylamide gel showing the molecular weights of recombinant α-N-acetylglucosaminidase polypeptides produced in CHO cells before (−) and after (+) PNGase F digestion. The 50 mM NaCl and 75 mM NaCl fractions are indicated.

SDS-PAGE of the two eluates showed two polypeptide bands associated with enzyme activity with apparent molecular weights of 79 and 89 kDa. The smaller α-N-acetylglucosaminidase was eluted predominantly in the 50 mM NaCl fraction whereas the 89 kDa α-N-acetylglucosaminidase polypeptide was enriched in the 75 mM NaCl fraction (FIG. 2).

The difference in apparent molecular weight of the recombinant α-N-acetylglucosaminidase polypeptides is due to the presence of additional carbohydrate side chains, since a digest with PNGase F, which cleaves off N-glycosylation groups, reduced both the 79 kDa and 89 kDa polypeptides to the polypeptide band having an apparent molecular weight of about 70 kDa (FIG. 2), which corresponds to the approximate molecular weight deduced from primary amino acid sequence data (SEQ ID No:2).

EXAMPLE 9

Characteristics of Recombinant α-N-acetylglucosaminidase

No differences were observed between the enzyme activities of the 79 and 89 kDa recombinant α-N-acetylglucosaminidase polypeptides produced in CHO cells according to Example 7 and 8. With the fluorogenic N-acetylglucosamine α-linked to 4-methylumbelliferone (4-MU) substrate, the enzyme has a pH-optimum of 4.6 with a $k_M$ of 5.34 mM and a $V_{max}$ of $3.97 \times 10^6$ pmol/min/mg. Towards a $^3$H-labelled disaccharide substrate it should a pH-optimum of 4.1 with a $k_M$ of 0.0166 mM and a $V_{max}$ of $4.48 \times 10^4$ pmol/min/mg.

EXAMPLE 10

Mutational Analysis of Sanfilippo B Patients

Genomic DNA is isolated from cultivated skin fibroblasts of patients by extraction with Phenol/Chloroform and used to amplify the eight exons and adjacent intronic sequences individually by PC.

Primer sequences used in the amplification reaction are readily determined from the nucleotide sequences of the α-N-acetylglucosaminidase cDNA and genomic clones.set forth in SEQ ID No:1 or SEQ ID No:3. Amplification conditions are also readily determined without undue experimentation.

Procedures for the design of PCR primers and amplification conditions are described in detail, for example, by McPherson et al. (1991). Differences in the primary sequence can be identified by separating the PCR products on a polyacrylamide gel under non-denaturing conditions (SSCP gels). Base changes, insertions and deletions will lead to a different band pattern compared with the wildtype in most of the cases, which can be visualised either by autoradiography of the gel after labelling the DNA during the PCR or by staining unlabelled DNA in the gel with silver. PCR products which show a different band pattern are sequences to identify the change. Other patient samples can be tested for mutations and polymorphism that were found by hybridisation with wildtype- and mutation-specific oligonucleotides (ASO).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

1. Ausubel, F. M., Brent, R., Kingston, R E, Moore, D. D., Seidman, J. G., Smith, J. A., and Struhl, K. (1987). In: Current Protocols in Molecular Biology. Wiley Interscience (ISBN 047150338).
2. Hopwood J J (1989) In: "*Heparin: Chemical and Biological Properties, Clinical Applications*" (Lane D W and Lindahl U, eds.), 190-229, Edward Arnold, London.
3. McKusick V and Neufeld E (1983) In: "*The Metabolic Basis of Inherited Disease*" (Stanbury J B, Wyngaarden J B, Fredrickson D S, Goldstein J L and Brown M S, eds), 5th Ed., 751-771, McGraw-Hill, New York.
4. McPherson, M. J., Quirke, P. and Taylor, G. R, (1991) In: PCR A Practical Approach. Oxford University Press, Oxford. (ISBN 0-19-96322L-X).
5. O'Brien J S, (1972) *Proc. Natl. Acad. Sci. USA* 69: 1720-1722.
6. Sambrook, J., Fritsch, E., and Maniatis, T. (1989) In: "Molecular Cloning" a laboratory manual, Cold Spring Harbour.
7. Von Figura, K, and Kresse H, (1972) *Biochem Biophys. Res. Commun,* 48: 262-269
8. Weber B, Scott H, Blanch L, Clements P, Morris C P, Anson D, Hopwood J, (1996) Nature Genetics (submitted)

What is claimed is:

1. A method for the production of α-N-acetylglucosaminidase, said method comprising:
   (i) transfecting mammalian cells with an expression vector comprising a DNA molecule encoding α-N-acetylglucosaminidase having the amino acid sequence of SEQ ID NO:2 or fragment thereof comprising amino acids 24-743 of SEQ ID NO:2 fused to a signal sequence;
   (ii) culturing the transfected cells, whereby the α-N-acetylglucosaminidase protein having the amino acid sequence of SEQ ID NO:2 or fragment thereof comprising amino acids 24-743 of SEQ ID NO:2 fused to a signal sequence is produced and α-N-acetylglucosaminidase protein secreted into the medium; and
   (iii) recovering the α-N-acetylglucosaminidase protein, from the medium.

2. The method according to claim 1, wherein the DNA molecule encoding α-N-acetylglucosaminidase is the cDNA having the sequence SEQ ID NO:1.

3. The method according to claim 1 wherein the mammalian cells are CHO cells.

4. The method according to claim 1 wherein the protein recovered from the medium is in a glycosylated form.

5. The method according to claim 4 wherein the molecular weight of the glycosylated form of the protein recovered from the medium as determined using SDS/PAGE is at least approximately 79 kDa.

* * * * *